United States Patent
Kido

(10) Patent No.: US 10,304,176 B2
(45) Date of Patent: May 28, 2019

(54) IMAGE INSPECTION DEVICE

(71) Applicant: Keyence Corporation, Osaka (JP)

(72) Inventor: Manabu Kido, Osaka (JP)

(73) Assignee: Keyence Corporation, Osaka (JP)

( * ) Notice: Subject to any disclaimer, the term of this patent is extended or adjusted under 35 U.S.C. 154(b) by 0 days.

(21) Appl. No.: 15/925,805

(22) Filed: Mar. 20, 2018

(65) Prior Publication Data

US 2018/0330490 A1 Nov. 15, 2018

(30) Foreign Application Priority Data

May 9, 2017 (JP) .................................. 2017-093357

(51) Int. Cl.
| | |
|---|---|
| *H04N 7/18* | (2006.01) |
| *G06T 7/00* | (2017.01) |
| *H04N 5/225* | (2006.01) |
| *H04N 5/232* | (2006.01) |

(52) U.S. Cl.
CPC .......... *G06T 7/0004* (2013.01); *H04N 5/2256* (2013.01); *H04N 5/23293* (2013.01); *G06T 2207/10152* (2013.01); *G06T 2207/30164* (2013.01)

(58) Field of Classification Search
CPC ........ H04N 7/18; H04N 5/225; H04N 5/2256; H04N 5/232; H04N 5/23293; G06T 7/00; G06T 7/0004; G06T 3/00; G06T 3/0081; G06T 2207/10152; G06T 2207/30164
USPC ........................... 348/131; 382/152; 356/237
See application file for complete search history.

(56) References Cited

U.S. PATENT DOCUMENTS

| | | | | |
|---|---|---|---|---|
| 7,570,369 B2 * | 8/2009 | Henrikson | ............. | G01B 11/24 250/559.36 |
| 8,363,214 B2 * | 1/2013 | Watanabe | ............. | G01B 11/30 356/237.2 |
| 8,472,019 B2 * | 6/2013 | Seo | .......................... | G01J 3/02 356/328 |
| 8,493,558 B2 * | 7/2013 | Asada | .................. | G01N 21/255 356/237.1 |

(Continued)

FOREIGN PATENT DOCUMENTS

JP H09-126890 5/1997

OTHER PUBLICATIONS

U.S. Appl. No. 15/925,804, filed Mar. 20, 2018 (75 pages).

(Continued)

*Primary Examiner* — Trang U Tran
(74) *Attorney, Agent, or Firm* — Kilyk & Bowersox, P.L.L.C.

(57) ABSTRACT

The invention alleviates a burden on a user relating to selection of a lighting color required for image inspection by multi-spectral imaging. A processor controls an illumination device to irradiate a setting target object individually with an illumination beam of each lighting color in a predetermined order, thereby generating a plurality of spectral images. The processor sets a combination of lighting colors recommended to illuminate an inspection target object based on the plurality of spectral images. An inspection unit inspects the inside of each inspection region in a plurality of inspection images generated for the inspection target object illuminated by illumination beams of lighting colors according to the set combination of recommended lighting colors.

15 Claims, 21 Drawing Sheets

(56) References Cited

U.S. PATENT DOCUMENTS 9,759,665 B2* 9/2017 Ahn .................... G01N 21/95
9,795,996 B2* 10/2017 Adams ................ B07C 5/3425

OTHER PUBLICATIONS

U.S. Appl. No. 15/925,803, filed Mar. 20, 2018 (100 pages).
U.S. Appl. No. 15/925,802, filed Mar. 20, 2018 (85 pages).
U.S. Appl. No. 15/925,801, filed Mar. 20, 2018 (74 pages).

* cited by examiner

IMAGE INSPECTION DEVICE

CROSS-REFERENCE TO RELATED APPLICATIONS

The present application claims foreign priority based on Japanese Patent Application No. 2017-093357, filed May 9, 2017, the contents of which is incorporated herein by reference.

BACKGROUND OF THE INVENTION

1. Field of the Invention

The present invention relates to an image inspection device using multi-spectral imaging.

2. Description of Related Art

Image inspection devices that inspect an image obtained by capturing an image of a workpiece to determine whether a product (workpiece) has been produced as designed are extremely useful. A shape, a size, a color, and the like of the workpiece are inspected in such image inspection. JP H09-126890 A proposes a color detecting apparatus which captures an image of an inspection target object such as a printed matter to acquire color information and executes color inspection with high accuracy.

Meanwhile, desired color information is realized by selecting a wavelength by a color filter on a camera side or selecting a wavelength of an illumination beam. For example, it is conceivable to irradiate a workpiece with white light by a white light source and to select reflected light of a desired wavelength out of the light reflected from the workpiece by a spectral optical system. This may be realized by using an imaging element including a plurality of color filters having different pass wavelengths. When an RGB color filter is used, an R image, a G image, and a B image can be obtained. Similarly, an R image may be acquired by irradiating a workpiece with a red illumination beam by a red LED, a G image may be acquired by irradiating the workpiece with a green illumination beam by a green LED, and a B image may be acquired by irradiating the workpiece with a blue illumination beam by a blue LED. The latter imaging method is called multi-spectral imaging, and basically, each color LED is alternatively turned on. Further, a large number of spectral images can be obtained when a large number of light sources having mutually different wavelengths are employed so that even a subtle color difference can be discriminated. Meanwhile, as the number of wavelengths becomes larger, the inspection time becomes longer.

Not all of such a large number of wavelengths are always required for image inspection. For example, sufficient inspection accuracy may be obtained by using only four of eight wavelengths.

However, it is not easy for a user to select a wavelength to be used for inspection. Therefore, an object of the present invention is to alleviate a burden on the user relating to selection of a wavelength that is required for image inspection using multi-spectral imaging.

SUMMARY OF THE INVENTION

For example, an image inspection device of the present invention includes: an illumination unit which includes a plurality of light emitting elements that generate illumination beams mutually having different lighting colors and individually irradiates a target object with the illumination beams of the respective lighting colors; an imaging unit which receives light reflected from the target object for each of the illumination beams of the lighting colors and generates a spectral image of the target object; a control unit which controls the illumination unit to irradiate the target object sequentially with the illumination beams of the respective lighting colors and controls the imaging unit to generate a plurality of the spectral images; a display unit which displays an image of the target object based on the plurality of spectral images of the target object; a region reception unit which receives designation of a foreground region and a background region in the image of the target object displayed on the display unit; a specifying unit which specifies color information of a foreground color based on color information of a pixel in the foreground region and specifies color information of a background color based on color information of a pixel in the background region; a setting unit which calculates a separation degree between the color information of the foreground color and the color information of the background color for each of combinations of lighting colors recommended for illumination of an inspection target object out of the plurality of lighting colors, and sets a combination of recommended lighting colors based on the separation degree; and an inspection unit which inspects an inside of an inspection region in an inspection image generated for the inspection target object illuminated by illumination beams of lighting colors according to the combination set by the setting unit.

According to the present invention, a combination of wavelengths suitable for the inspection target object is decided by the image inspection device, and thus, a burden on a user relating to wavelength selection is alleviated.

DETAILED DESCRIPTION OF PREFERRED EMBODIMENT

One embodiment of the present invention will be described below. Individual embodiments to be described below will be useful for understanding various concepts of the present invention such as superordinate concepts, intermediate concepts, and subordinate concepts. In addition, it should be understood that the technical scope of the present invention is defined by the scope of the claims and is not limited by the individual embodiments below.

Figure 1:
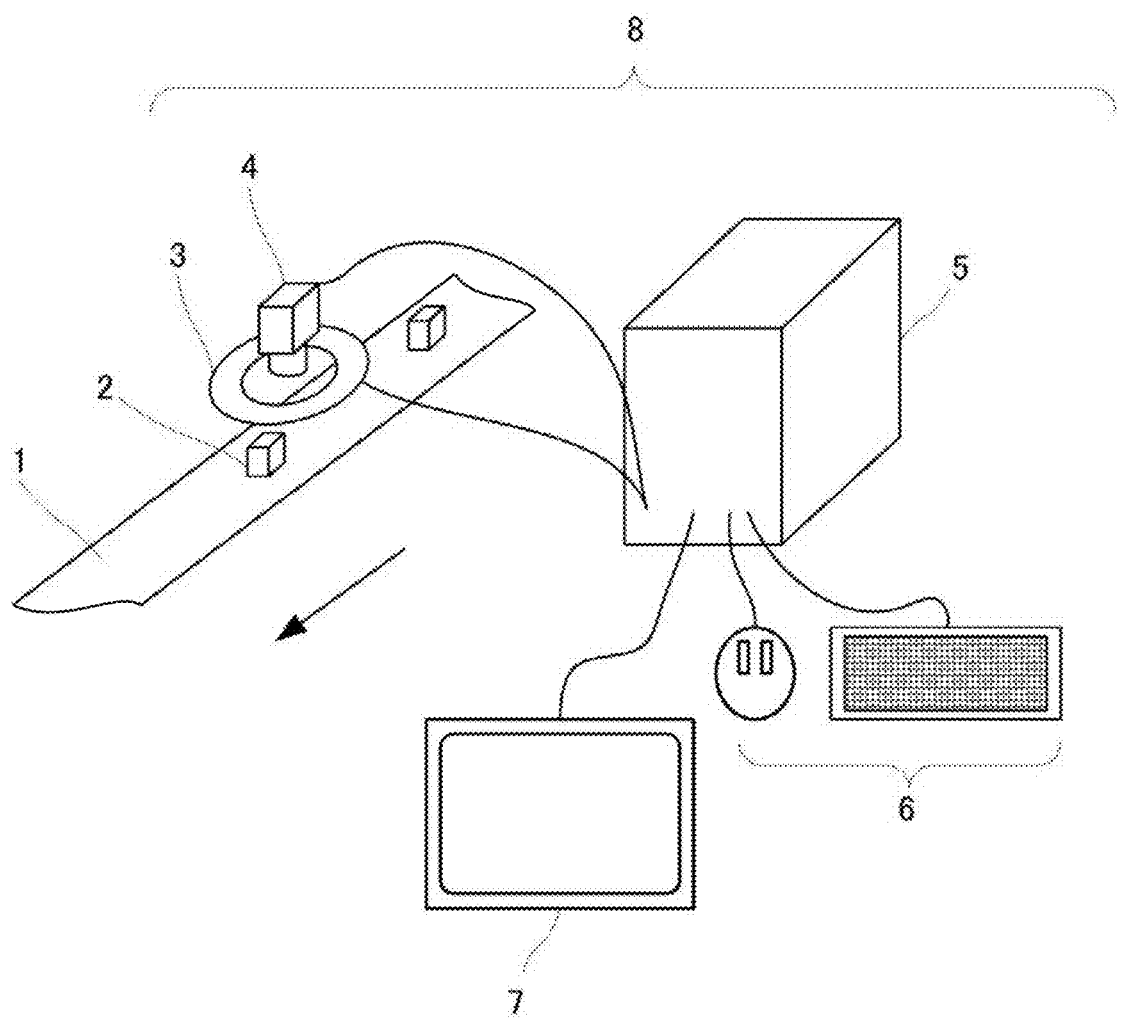
FIG. 1 is a view illustrating an image inspection device.

FIG. 1 is a view illustrating an example of a visual inspection system (image inspection device 8). A line 1 is a conveyor belt or the like for conveying a workpiece 2 which is an inspection target object. An illumination device 3 is an example of an illumination unit which includes a plurality of light emitting elements that generate inspection light (illumination beams) of mutually different wavelengths, and individually irradiates the target object with the illumination beam of each wavelength. A plurality of light emitting elements having the same wavelength may be provided in order to irradiate the workpiece 2 with the illumination beam simultaneously or sequentially from a plurality of directions. A camera 4 is an example of an imaging section for receiving light reflected from the inspection target object illuminated by the illumination beam and generating a luminance image (spectral image). An image processing device 5 includes an inspection unit which illuminates the inspection target object to be subjected to image inspection by sequentially turning on the light emitting elements at illumination intensity set for each wavelength, and executes the image inspection using a plurality of inspection images acquired by the imaging unit. A display unit 7 is a display device which displays a user interface for setting a control parameter relating to the inspection, the inspection images, and the like. An input unit 6 is a console, a pointing device, a keyboard, or the like, and is used to set the control parameter.

<Configuration of Illumination Device>

Figure 2A:
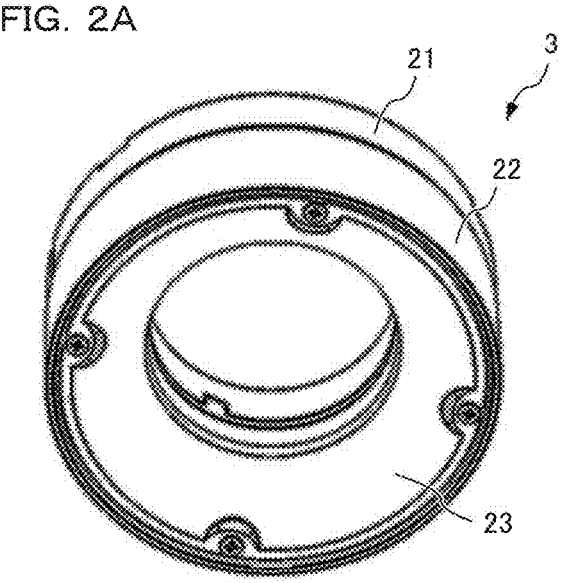
FIGS. 2A to 2D are views illustrating an illumination device.
Figure 2B:
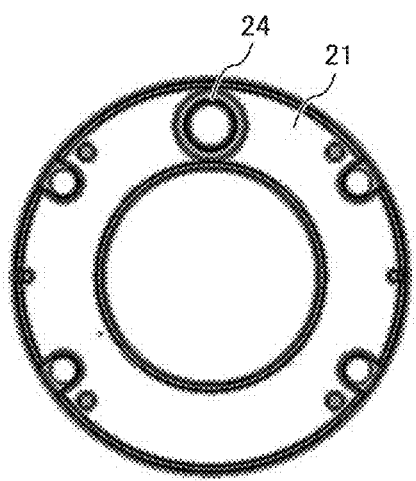
Figure 2C:
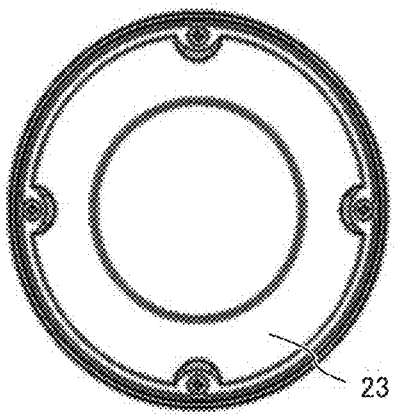
Figure 2D:
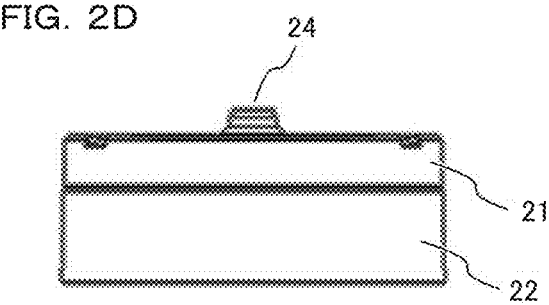

FIG. 2A is a perspective view of the illumination device 3. FIG. 2B is a top view of the illumination device 3. FIG. 2C is a bottom view of the illumination device 3. FIG. 2D is a side view of the illumination device 3. A casing of the illumination device 3 includes an upper case 21 and a lower case 22. A light diffusing member 23 which diffuses light output from each of a plurality of light sources (light emitting elements such as LEDs) is arranged at a lower part of the lower case 22. As illustrated in FIGS. 2A and 2C, the light diffusing member 23 also has an annular shape similarly to the upper case 21 and the lower case 22. As illustrated in FIGS. 2B and 2D, a connector 24 is provided on an upper surface of the upper case 21. A cable for communication between an illumination control board housed in the illumination device 3 and the image processing device 5 is connected to the connector 24.

Figure 3A:
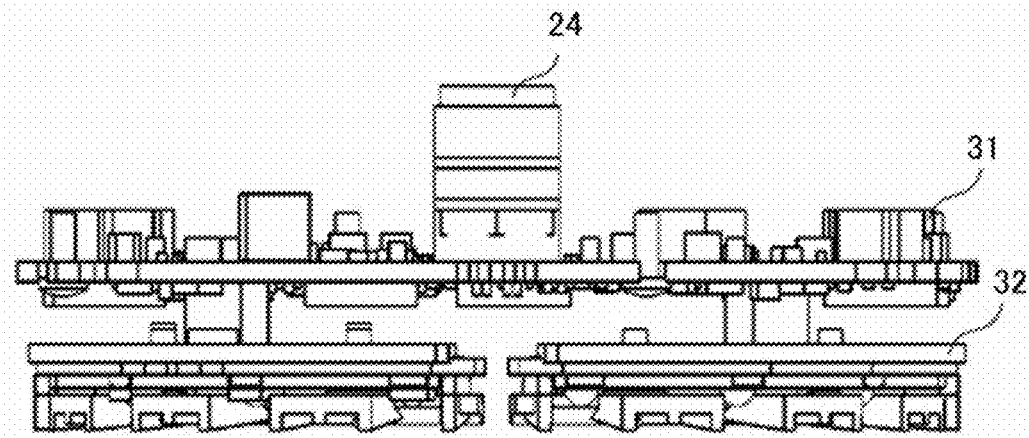
FIGS. 3A to 3E are views illustrating parts constituting the illumination device.
Figure 3B:
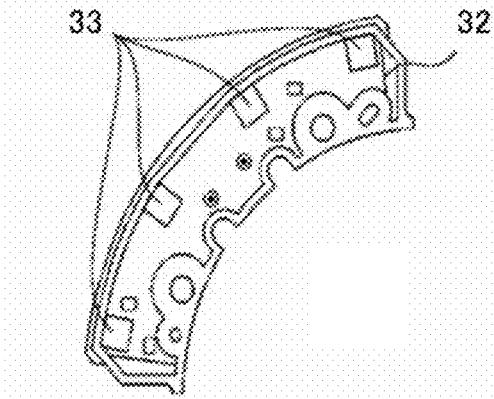
Figure 3C:
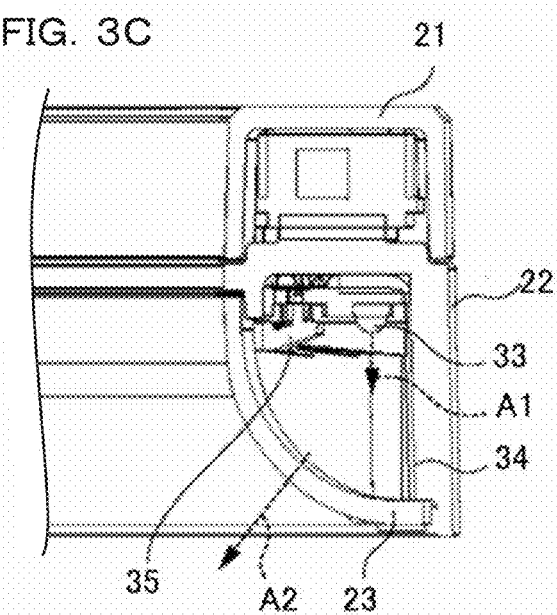
Figure 3D:
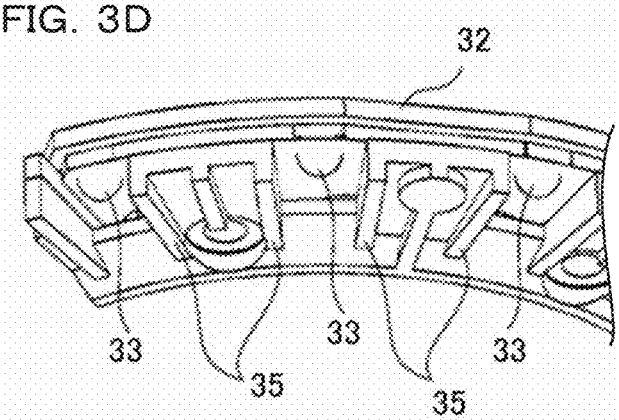
Figure 3E:
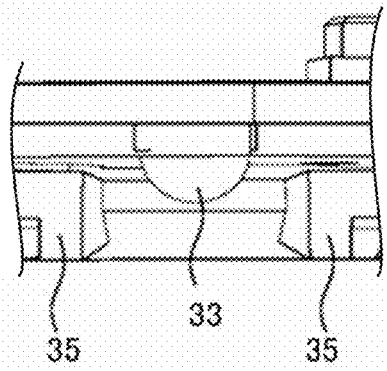

FIG. 3A is a side view illustrating a control board 31 and an LED board 32 housed in the illumination device 3. The control board 31 is an example of a second board on which a lighting control unit is mounted. The LED board 32 is an example of a first board on which the plurality of light sources are mounted. FIG. 3B is a top view of the LED board 32. FIG. 3C is an enlarged cross-sectional view of the vicinity of an LED 33 in the illumination device 3. FIG. 3D is a bottom view of the LED board 32. FIG. 3E is an enlarged side view of the vicinity of the LED 33 in the LED board 32.

The illumination control board and the connector 24 are arranged on the control board 31. The light emitting elements such as LEDs constituting a light source group are mounted on the LED board 32. As illustrated in FIG. 3B, four LED boards 32 are provided for irradiation of the illumination beam from four directions in the present embodiment. That is, one LED board 32 forms one illumination block. As the irradiation of the illumination beam from the four directions is possible, it is possible to acquire a photometric stereo image. That is, the illumination device 3 may be used not only for multi-spectral imaging (MSI) but also for photometric stereo. In a case where four LEDs 33 are arranged on the one LED board 32, the light source group is constituted by sixteen light emitting elements. Meanwhile, a larger number of light emitting elements may be provided. For example, eight LEDs 33 may be arranged on the one LED board 32, and wavelengths of light emitted by the eight LEDs 33 may be different from each other. As illustrated in FIGS. 3C, 3D, and 3E, a light shielding member 35 is arranged between the two adjacent LEDs 33 among the plurality of LEDs 33. When a large number of the LEDs 33 are closely arranged, illumination beams irradiated, respectively, from the two adjacent LEDs 33 may pass through the same region of the light diffusing member 23 in some cases. In this case, the surface of the workpiece 2 is irradiated with the illumination beams with the same amount of light from the same illumination direction in both of a case where one of the LEDs 33 is turned off and the other LED 33 is turned on and a case where the other LED 33 is turned off and the one LED 33 is turned on according to a lighting pattern. Then, it is difficult to generate the inspection images with high accuracy. Thus, a balance between uniformity of the amount of light and independence of the light source is obtained for the two adjacent LEDs 33 by arranging the light shielding member 35 between the two adjacent LEDs 33. As illustrated in FIG. 3C, a light emission direction A1 of the LED 33 does not coincide with a main illumination direction A2. Thus, the light emitted from the LED 33 is deflected toward the light diffusing member 23 by arranging a reflector 34. As a result, it is possible to efficiently irradiate the workpiece 2 with the light emitted from the LED 33. The emission direction A1 and a reflection direction of the reflector 34 are substantially orthogonal to each other in this example since a cross-sectional shape of the light diffusing member 23 forms an arc (FIG. 3C)) and an angle (central angle) of the arc is about 90 degrees. As the central angle is set large in this manner, it is easy to irradiate the surface of the workpiece 2 with substantially uniform parallel light even if the illumination device 3 is moved away from or close to the workpiece 2.

Figure 21:
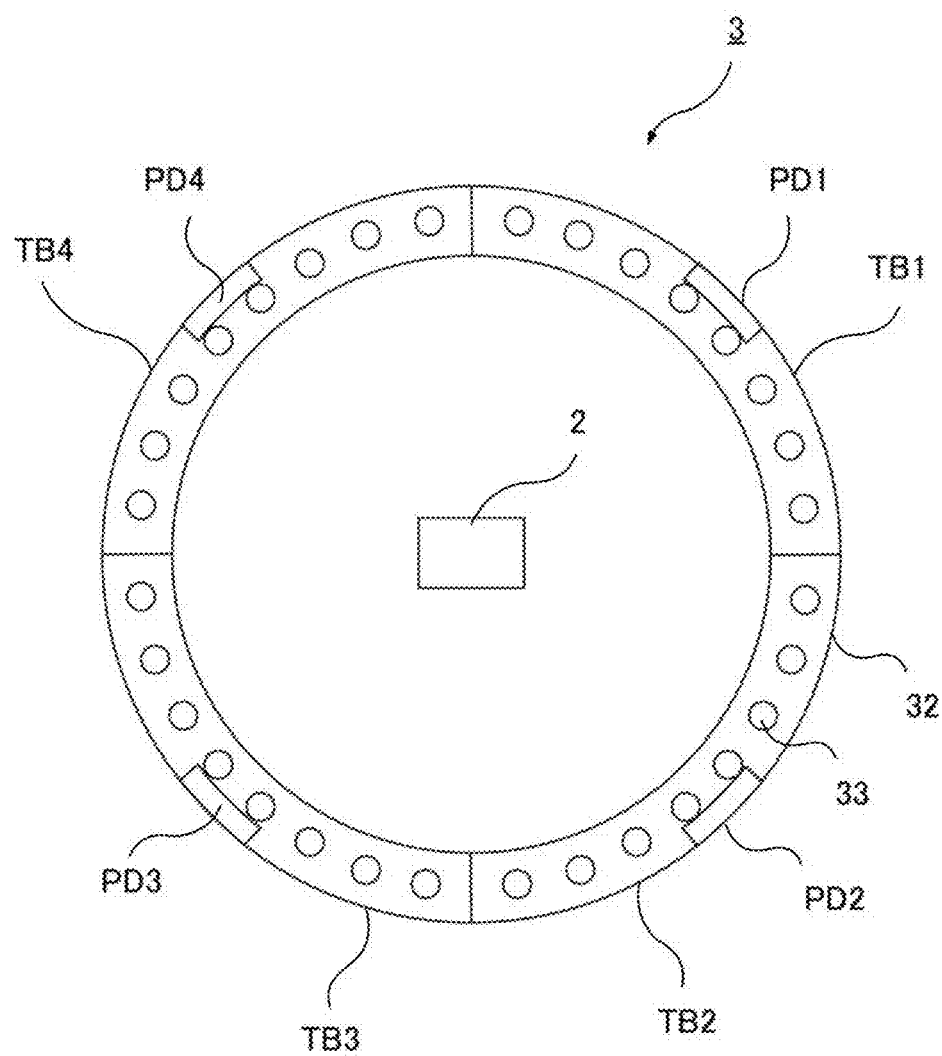
FIG. 21 is a view illustrating the illumination device.

FIG. 21 is a schematic plan view of the illumination device 3. The plurality of LEDs 33 that emit light of mutually different wavelengths are arranged in an annular shape on the LED board 32 of the illumination device 3. The illumination control board (FIG. 4) provided on the control board 31 simultaneously turns on the plurality of LEDs 33 having the same wavelength. The plurality of LEDs 33 having the same wavelength are arranged on the LED board 32 at equal intervals. As the plurality of LEDs 33 having each wavelength are simultaneously turned on, the workpiece 2 is irradiated with the substantially uniform illumination beam from an obliquely upper side of the workpiece 2. Accordingly, the camera 4 can capture an omni-directional illumination image of the workpiece 2 corresponding to the respective wavelengths that does not depend on an irradiation direction.

The illumination device 3 is constituted by four illumination blocks TB1 to TB4 each of which includes the plurality of LEDs 33. The plurality of LEDs 33 that emit light of mutually different wavelengths are arranged in each illumination block. Each illumination block includes the LEDs 33 of all wavelength types provided in the illumination device 3. Light receiving elements PD1 to PD4 for light amount feedback control are arranged in each illumination block. The illumination control board controls a current value to be supplied to each of the LEDs 33 such that a light amount of each illumination block is maintained at a light amount set in advance based on a receiving amount of light received by the light receiving elements PD1 to PD4.

The LEDs 33 of the respective wavelengths are arranged in the same number and at equal intervals in the respective illumination blocks. In the example illustrated in FIG. 21, the LEDs 33 of eight wavelengths are arranged one by one at equal intervals in each illumination block. Each illumination block may include two or more LEDs 33 of the same wavelength. In this case, each illumination block is provided with a multiple of the number of wavelengths, for example, 16 (8 wavelengths×2), 24 (8 wavelengths×3), or 32 (8 wavelengths×4) LEDs 33. The plurality of LEDs 33 having the same wavelength are arranged at equal intervals in each illumination block. The above-described arrangement of the LEDs 33 is common to all the illumination blocks. A ring-type illumination is configured by arranging the plurality of illumination blocks in an annular shape. That is, the LEDs 33 having the same wavelength are arranged at equal intervals in the annular shape.

The illumination control board can perform individual lighting control of the illumination device 3 in units of wavelengths. When the LED 33 of a single wavelength, for example, red is turned on, the illumination control board simultaneously turns on the red LEDs 33 included in all the illumination blocks. By sequentially turning on the LEDs 33 of each wavelength, the illumination control board can irradiate the workpiece 2 sequentially with light of different wavelengths. In addition, the illumination control board can perform individual lighting control of each illumination block. For example, the illumination control board may turn on the LEDs 33 included in the illumination block TB1 and turn off the LEDs 33 included in the illumination blocks TB2 to TB4. In addition, the illumination control board can also turn on the illumination blocks TB1 to TB4 sequentially (in the order of TB1, TB2, TB3, TB4). By switching the illumination block to be turned on by the illumination control board, a plurality of luminance images of the workpiece 2 illuminated from different directions may be acquired and used for inspection. Further, the illumination control board can also perform individual lighting control of the LED 33 in units of both wavelengths and illumination blocks. For example, the illumination control board can turn on only the red LED 33 included in the illumination block TB1.

By performing the lighting control of the LEDs 33 in units of wavelengths in this manner, the illumination device 3 irradiates the workpiece 2 with light of different wavelengths. In addition, by performing the lighting control of the LEDs 33 in units of the respective illumination block, it is possible to irradiate the workpiece 2 with light from different irradiation directions.

Not only the monochromatic LED 33 but also the white LED 33 that emits white light in which beams of a plurality of wavelengths are mixed may be arranged on the control board 31. The illumination control board may selectively turn on only the white LED 33 so that the illumination device 3 in the present embodiment is made to function in the same manner as a typical white ring illumination. Further, the illumination control board can also irradiate the workpiece 2 with substantially the white light by simultaneously turning on the LEDs 33 of all wavelengths.

In the present specification, the image obtained by the illumination control board irradiating the workpiece 2 with the illumination beam of the monochromatic wavelength is called a spectral image. In addition, the image obtained by turning on the LEDs 33 of all wavelengths or turning on the white LED 33 is distinguished from the spectral image and is called a white image. The spectral image and the white image may be collectively referred to as the luminance image. Each pixel of the luminance image indicates a luminance value obtained from the camera 4.

Each illumination block is provided with the illumination control board. When each illumination block includes the plurality of LEDs 33 having the same wavelength, the LEDs 33 having the same wavelength are connected in series to each illumination control board, and the LEDs 33 having different wavelengths are connected in parallel.

According to the above drawings, the plurality of LEDs 33 are arranged on a certain circumference, but the plurality of LEDs 33 may be also arranged on another circumference having a different radius. As a result, the number of LEDs 33 for each wavelength increases so that it is possible to increase the amount of illumination light. In addition, the LEDs 33 for multi-spectral imaging may be arranged on a first circumference and the white LED may be arranged on a second circumference. A radius of the first circumference is different from a radius of the second circumference.

<Circuit Configuration of Illumination Device>

Figure 4:
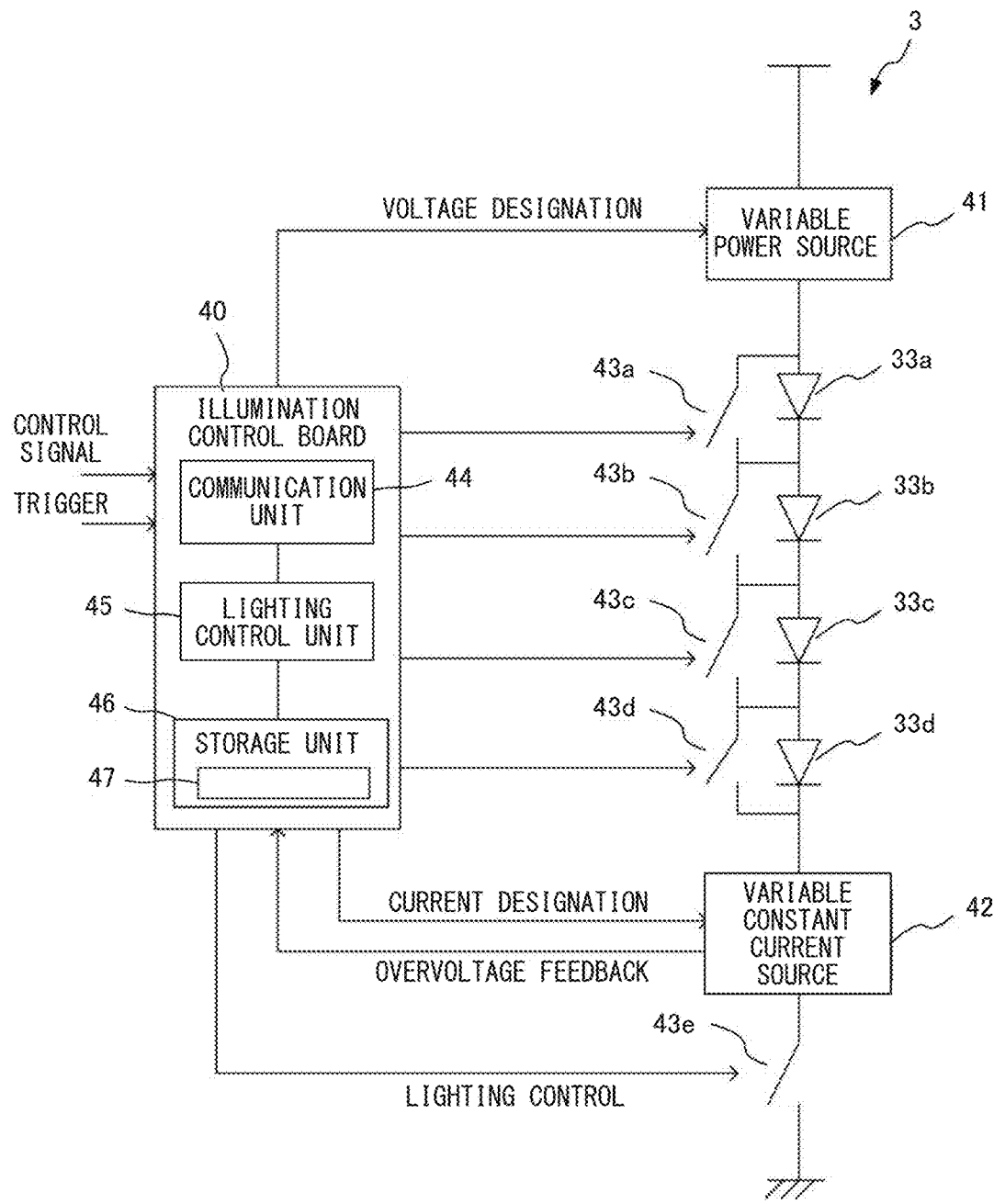
FIG. 4 is a diagram illustrating an electrical configuration of the illumination device.

FIG. 4 illustrates an example of a circuit configuration of the illumination device 3. In this example, one illumination block out of the four illumination blocks constituting the light source group is illustrated, and each illumination block is provided with four LEDs (LED 33a to LED 33d) having the same wavelength. The four LEDs 33a to 33d are connected in series. LEDs having different wavelengths connected in series in the same manner are connected in parallel with the circuit configuration of FIG. 4, but are not illustrated in FIG. 4. A variable power source 41 with a variable voltage generates and outputs a voltage having a voltage value (for example, 2 V to 20 V) designated by an illumination control board 40. A variable constant current source 42 adjusts a current flowing in the illumination block so as to have a current value (for example, 0 A to 1 A) designated by the illumination control board 40. As such a current control system is employed, it is easy to realize dimming with high linearity. In addition, the variable constant current source 42 detects a value of a voltage applied to the variable constant current source 42 and performs feedback to the illumination control board 40, thereby protecting the variable constant current source 42 from an overvoltage. Switches 43a to 43d are connected in parallel to the LEDs 33a to 33d, respectively. A lighting control unit 45 of the illumination control board 40 can individually switch on and off of each of the LEDs 33a to 33d by individually opening and closing these switches 43a to 43d. As the switches 43a to 43d are connected in parallel to the LEDs 33a to 33d, respectively, in this manner, it is possible to perform the individual lighting by turning on any one of the LEDs 33a to 33d or turning on all of the LEDs 33a to 33d. This is useful for realizing various lighting patterns. The lighting control unit 45 executes the lighting control in the unit of one illumination block by switching on/off of a main switch 43e inserted between the variable constant current source 42 and a ground. A communication unit 44 receives a control signal to instruct a lighting pattern and a trigger signal to instruct start of lighting from an illumination control unit of the image processing device 5, and sends the signals to the lighting control unit 45. The lighting control unit 45 reads lighting pattern data 47 corresponding to the control signal from a storage unit 46 and controls the switches 43a to 43d according to the lighting pattern data 47. Eight switches 43 are provided when one illumination block is constituted by eight LEDs 33, and the eight switches 43 are controlled by the lighting control unit 45. For example, the eight LEDs 33 correspond to eight wavelengths from UV to IR2. UV represents a spectral image acquired by an illumination beam of an ultraviolet wavelength. B represents a spectral image acquired by an illumination beam of a blue wavelength. G represents a spectral image acquired by an illumination beam of a green wavelength. AM represents a spectral image acquired by an illumination beam of an amber wavelength. OR represents a spectral image acquired by an illumination beam of an orange wavelength. R represents a spectral image acquired by an illumination beam of a red wavelength. IR1 and IR2 represent spectral images acquired by illumination beams of infrared wavelengths. Here, the wavelength of IR1 is shorter than the wavelength of IR2.

<Functional Block>

Figure 5:
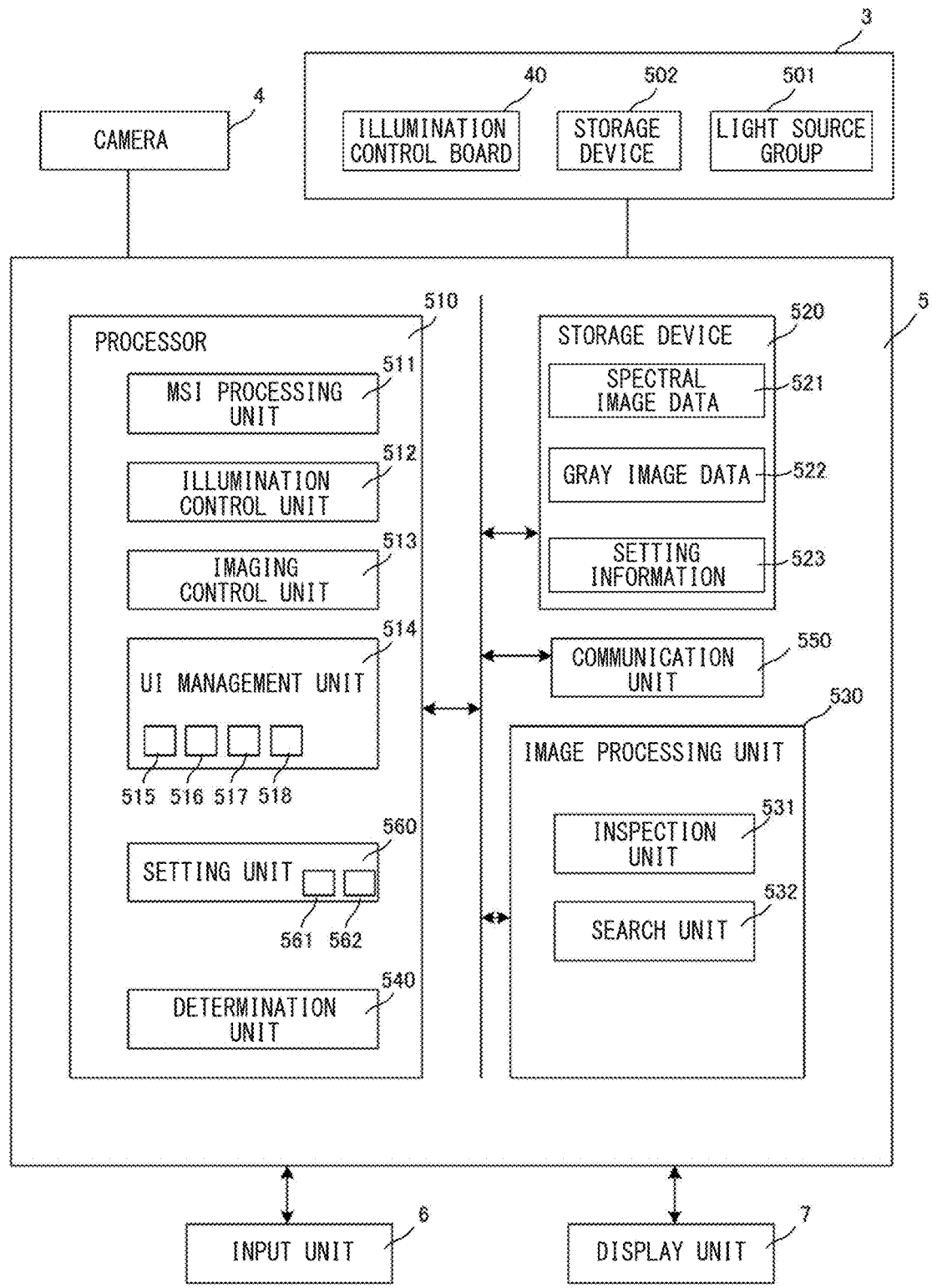
FIG. 5 is a diagram illustrating functions of an image processing system.

FIG. 5 is a block diagram of an inspection device. In this example, the illumination device 3, the camera 4, and the image processing device 5 are housed in individual casings, respectively, but this is merely an example, and the integration thereof may be obtained as appropriate. The illumination device 3 is the illumination device that realizes the multi-spectral imaging, but may be used as an illumination section that illuminates an inspection target object according to a photometric stereo method. The illumination device 3 includes a light source group 501 and the illumination control board 40 that controls the light source group 501. As already illustrated in FIGS. 3A to 3E, one illumination block may be constituted by the plurality of light emitting elements, and the light source group 501 may be constituted by the plurality of illumination blocks. The number of illumination blocks is generally four, but may be three or more. This is because it is possible to generate an inspection image by the photometric stereo method if the workpiece 2 can be irradiated with illumination beams from three or more illumination directions. Each illumination block is provided with the plurality of light emitting elements (LEDs 33) that output illumination beams having different lighting colors, respectively. The plurality of light emitting elements may include the white LED. The white LED is not used for the multi-spectral imaging but can be used to create another inspection image and to create an image for movement correction of the workpiece 2. As illustrated in FIGS. 1 and 3A to 3E, an outer shape of the illumination device 3 may have a ring shape. In addition, the illumination device 3 may be constituted by a plurality of illumination units separated from each other. The illumination control board 40 controls a lighting timing and an illumination pattern (lighting pattern) of the light source group 501 according to a control command received from the image processing device 5. The workpiece 2 is irradiated with illumination beams of alternately selected lighting colors when acquiring the spectral image by the multi-spectral imaging, but may be irradiated simultaneously with the illumination beams of a plurality of lighting colors when a method other than the multi-spectral imaging is adopted. The illumination control board 40 has been described as being built in the illumination device 3, but may be built in the camera 4 or the image processing device 5, or may be housed in a casing independent therefrom.

A storage device 502 is built in the illumination device 3, and the lighting timing and the illumination pattern of the light source group 501 set by the user are stored therein. The illumination control board 40 can receive the trigger signal from the image processing device 5 and control the light source group 501 according to contents stored in the storage device 502. With this configuration, the image processing device 5 can control the illumination device 3 only by transmitting the trigger signal, and thus, it is possible to reduce the number of signal lines that connect the image processing device 5 and the illumination device 3, thereby improving the handling of cables.

More specifically, the storage device 502 stores illumination setting data that includes lighting timing information (a lighting time and a lighting interval), illumination intensity information, illumination pattern information (identification information of a wavelength to be turned on), and illumination block information (identification information of a block to be turned on) of the light source group 501 of each wavelength. All of the illumination setting data causes the user interface for illumination setting to be displayed on the display unit 7, and an illumination setting section receives adjustment made by the user.

The lighting timing information is information that defines a lighting timing of each wavelength when the light source group corresponding to each wavelength is periodically turned on, and includes the lighting time (pulse width) in which the light source group of each wavelength is turned on, and the lighting interval (interval) from turning-on of the light source group of a previous wavelength to turning-on of the light source group of a next wavelength at the time of switching the wavelength to be turned on. For example, when the user performs inspection using a light source group emitting red and green light, the user can set a lighting time of the light source group of a red wavelength, a lighting time of the light source group of a green wavelength, and an interval between both the lighting times. The user may individually set the lighting time of each wavelength, or the setting of the lighting time may be common to the entire wavelength. Regarding the setting of the lighting interval, the user may directly designate the lighting interval, or the lighting interval may be automatically calculated based on a length of one lighting cycle for sequentially turning on the light source group of the entire wavelength used for inspection and the lighting time of each wavelength.

The illumination intensity information is information that indicates the illumination intensity of each wavelength. The illumination intensity of each wavelength can be individually set in the present embodiment, and thus, it is possible to irradiate the workpiece with light with an optimum illumination intensity at each wavelength.

The illumination pattern information is identification information that indicates a type of the wavelength to be turned on, and is information used to decide which light source group corresponding to which wavelength needs to be turned on at each lighting timing. For example, when the user performs setting of inspection using three colors of red, green, and purple, the storage device 502 stores the identification information indicating these three wavelengths in association with the information on each lighting timing (lighting pulse). For example, the storage device 502 stores the illumination pattern information in association with the lighting timing information such that a red light source group is turned on with a first lighting pulse, a green light source group is turned on with a next lighting pulse, and a purple light source group is turned on with a last lighting pulse. Information indicating an order of lighting wavelengths may be included in the illumination pattern information. In the above example, the order of red, green, and purple may be set by the user, or a lighting order of wavelengths that can be set may be fixed and determined in advance. A storage device 520 of the image processing device 5 shares the illumination pattern information with the illumination device 3. In the above example, an image acquired first is processed as an image obtained with a red wavelength, an image acquired next is processed as an image obtained with a green wavelength, and an image acquired last is processed as an image obtained with a purple wavelength.

The illumination block information is identification information on the illumination block to be turned on. In the present embodiment, it is possible to individually control lighting in units of illumination blocks as well as to individually control lighting in units of wavelengths. The user can execute inspection using oblique illumination by arbitrarily selecting the illumination block to be turned on. In addition, it is also possible to generate a shape image using the principle of photometric stereo based on a plurality of luminance images obtained by illuminating light from different illumination directions by sequentially turning on all the illumination blocks. The user can also set an order of illumination blocks to be turned on. Illumination block to be turned on may be arbitrarily designated at each lighting timing, or a rotation direction of lighting (clockwise or counterclockwise) may fixed such that the user can designate an illumination block to be turned on first.

The illumination setting data set by the illumination setting section may be set from an input unit such as a personal computer (PC) connected to the illumination device 3 or from the image processing device 5 connected to the illumination device 3. In addition, the illumination device 3 may receive the setting via a controller for illumination which is provided separately from the image processing device 5. In addition, it is also possible to directly perform the illumination setting in an inspection device via the input unit 6 in the case of the inspection device in which the camera 4, the illumination device 3, and the image processing device 5 are integrally provided.

The storage device 502 is provided in the illumination device 3 in the above example, but may be provided in the image processing device 5. In addition, the storage device 502 may be provided in the camera 4 when the illumination device 3 and the camera 4 are integrally provided. When the illumination device 3, the camera 4, and the image processing device 5 are integrally provided in one housing, the storage device 502 is provided in the housing.

The camera 4 is an example of the imaging section that receives light reflected from the inspection target object illuminated by the illumination device 3 and generates the luminance image, and executes imaging processing according to the control command from the image processing device 5. The camera 4 may create a luminance image of the workpiece 2 and transfer the created luminance image to the image processing device 5, or a luminance signal obtained from an imaging element of the camera 4 may be transferred to the image processing device 5 so that the image processing device 5 may generate a luminance image. Since the luminance image is based on the luminance signal, the luminance signal is also the luminance image in a broad sense. In addition, the camera 4 functions as the imaging unit that receives the light reflected from the target object for each of illumination beams of the respective lighting colors output from the illumination device 3 and generates the image (spectral image) of the target object.

The image processing device 5 is a type of computer, and includes a processor 510 such as a CPU and an ASIC, the storage device 520 such as a RAM, a ROM, and a portable storage medium, an image processing unit 530 such as an ASIC, and a communication unit 550 such as a network interface. The processor 510 performs setting of an inspection tool, adjustment of the control parameter, generation of the inspection image, and the like. In particular, an MSI processing unit 511 creates a gray image of the workpiece 2 from a plurality of luminance images (spectral images) acquired by the camera 4 or creates an inspection image from the gray image according to multi-spectral imaging (MSI). The gray image itself may be the inspection image. An illumination control unit 512 controls the lighting pattern, an illumination switching timing, and the like by transmitting the control command to the illumination control board 40. That is, the illumination control unit 512 transmits a trigger signal to start illumination to the illumination device 3. An imaging control unit 513 transmits a trigger signal to start imaging in synchronization with the trigger signal issued from the illumination control unit 512 to the camera 4, thereby controlling the camera 4.

A UI management unit 514 displays a user interface (UI) for setting of the inspection tool, a UI for setting of a parameter required to generate the inspection image, and the like on the display unit 7, and sets the inspection tool and the parameter according to the information input from the input unit 6. The inspection tool may include a tool to measure a length of a specific characteristic (for example, a pin) provided in the workpiece 2, a tool to measure the area of the characteristic, a tool to measure a distance from a certain characteristic to another characteristic (for example, a pin interval) from one characteristic to another, a tool to measure the number of specific characteristics, a tool to inspect whether there is a flaw on a specific characteristic, and the like. In particular, the UI management unit 514 displays a UI for setting of a control parameter relating to multi-spectral imaging on the display unit 7. An image selection unit 515 reads image data of an image selected by the user through the UI from the storage device 520 and displays the image in an image display region inside the UI. A region designation unit 516 receives designation of an inspection region IW of the inspection tool and the like with respect to the displayed image from the user. In addition, the region designation unit 516 receives designation of a foreground region and a background region with respect to the displayed image from the user. The foreground region is a region from which a foreground color is extracted. The background region is a region from which a background color is extracted. The foreground color is often a color of a characteristic to be subjected to image inspection. The background color is a color that is distinguished from the foreground color. The foreground region, the background region, and the like are designated by the user, and thus, may be called designation regions. The region designation unit 516 may receive selection of a shape (for example, a rectangle, a circle, an ellipse, or an arbitrary shape) of the designation region and reflect a shape of a frame line indicating the designation region to the UI. A lighting color designation unit 517 is a lighting color reception unit which receives designation of a lighting color of an illumination beam from the user. In addition, the lighting color designation unit 517 is also a lighting color number reception unit which receives designation of the number of lighting colors of illumination beams from the user. The lighting color designation unit 517 may receive deletion or addition of lighting colors constituting combinations of the lighting colors. A threshold reception unit 518 receives a threshold for comparison with a measurement result acquired by the inspection tool of an inspection unit 531 in a determination unit 540, a threshold (tolerance) to be compared with each separation degree of combinations of a plurality of lighting colors, and the like from the user. The combination of lighting colors (lighting pattern) indicates a combination of light emitting elements, that is, the combination of lighting colors to be turned on. The UI management unit 514 saves these control parameters set by the user in setting information 523. The UI management unit 514 may function as a setting unit that sets an illumination condition and an imaging condition or as a setting unit that sets the inspection tool.

The image processing unit 530 includes the inspection unit 531, which executes various types of measurement by applying the inspection tool to the inspection image acquired by the multi-spectral imaging, and the like. A search unit 532 searches for a characteristic set before image inspection or a characteristic dynamically set during the image inspection within a search region SW arranged in the inspection image, and obtains a position of the found characteristic. The inspection unit 531 corrects a position of the inspection region (measurement region) according to the position of the found characteristic. The function of the image processing unit 530 may be implemented on the processor 510. Alternatively, the function of the processor 510 may be implemented on the image processing unit 530. In addition, the processor 510 and the processor 510 may implement a single function or a plurality of functions in cooperation with each other.

The determination unit 540 functions as a determination section for determining whether the workpiece 2 is non-defective/defective using the inspection image. For example, the determination unit 540 receives a result of the inspection performed using the inspection image in the image processing unit 530 and determines whether the inspection result satisfies a non-defective product condition (the tolerance or the like).

A setting unit 560 sets a combination of lighting colors to be recommended for illumination of the workpiece 2 out of the plurality of lighting colors based on a plurality of spectral images obtained by individually irradiating the workpiece 2 with illumination beams of the respective lighting colors in a predetermined order. As described above, the illumination device 3 includes at least N LEDs 33 that output the illumination beams of mutually different lighting colors. However, not all of the N LEDs 33 are required for inspection. For example, inspection accuracy considered to be necessary by the user may be achieved only by using the LEDs 33 corresponding to four lighting colors among the eight lighting colors. However, it is often difficult for the user to determine which of the eight lighting colors can be reduced. This is because a lighting color that is intuitively required and a lighting color that is actually required may not match. Thus, the setting unit 560 decides the combination of recommended lighting colors, which is a combination of the LEDs 33 (lighting colors) to be turned on, and proposes the determined combination to the user. A calculation unit 561 calculates the separation degree for each combination based on the plurality of spectral images corresponding to the respective combinations of the plurality of lighting colors. The separation degree is a distance between a color that is desirably extracted and another color that is desirably distinguished from the color in a color space. For example, the separation degree may be a distance between a distribution of a certain registered color, which has been registered in advance by the user, and a distribution of another registered color. In addition, the separation degree may be a distance between a color distribution in the foreground region and a color distribution in the background region. When there are a plurality of pieces of the color information, the separation degree may be an inter-group distance between a foreground group including color information of a plurality of foreground colors and a background group including color information of a plurality of background colors. A decision unit 562 decides a combination of recommended lighting colors based on the separation degree for each combination. For example, the decision unit 562 compares the separation degree for each combination, and decides a combination of lighting colors in which the maximum separation degree has been obtained as the combination of recommended lighting colors. In addition, the number (maximum number) of usable light emitting elements may be limited or designated by the user. This is because an inspection time that can be allocated to the single workpiece 2, conveyed by the line 1, is limited by conveying speed of the workpiece 2 and the like on the line 1. For example, there may be a case where the inspection can be completed within an upper limit value of the inspection time if four or less lighting colors are used, but the inspection cannot be completed within the upper limit value of the inspection time if five or more lighting colors are used. In this case, the four lighting colors become an upper limit number (maximum lighting-possible number M) of light emitting elements. Accordingly, the setting unit 560 decides combinations (lighting patterns) from N lighting colors to M or less lighting colors, obtains the separation degree for each combination, and decides the combination having the maximum separation degree as the combination of recommended lighting colors. The threshold reception unit 518 or the lighting color designation unit 517 receives the maximum lighting-possible number M, but may also receive a lower limit value of the separation degree. In general, as the separation degree is higher, the inspection accuracy becomes higher. However, the required inspection accuracy differs depending on the user and the characteristics of the workpiece 2. Accordingly, the setting unit 560 may decide a lighting pattern in which the separation degree equal to or higher than the lower limit has been obtained as the combination of recommended lighting colors among the combinations of the N lighting colors. In addition, the setting unit 560 may decide the lighting pattern in which the separation degree equal to or higher than the lower limit has been obtained as the combination of recommended lighting colors among the combinations of the M or less lighting colors. In addition, the setting unit 560 may decide a lighting pattern having a separation degree equal to or higher than the lower limit and the smallest number of lighting colors as the combination of recommended lighting colors among the combinations of the M or less lighting colors. In general, there is a trade-off relationship between the number of lighting colors and the inspection accuracy, and thus, the user decides the threshold used to decide the combination of recommended lighting colors, such as the maximum lighting-possible number M and the lower limit value of the separation degree. The plurality of inspection tools included in the inspection unit 531 may execute inspection (measurement) with respect to mutually different inspection regions. Thus, it is also considered that the combination of recommended lighting colors in which the maximum separation degree is obtained is different for each inspection tool. In this case, the setting unit 560 may decide the combination of recommended lighting colors such that all the separation degrees obtained for all the inspection tools selected by the user exceed the threshold. In addition, the separation degree of a combination of three lighting colors of R, G, and B may exceed the threshold in a certain inspection tool, but the separation degree of a combination of two lighting colors of R and IR1 may exceed the threshold in the other inspection tool. In this case, a combination of four lighting colors of R, G, B, and IR1, which is a logical sum of the combination of recommended lighting colors, may be decided as the combination of recommended lighting colors. In this manner, the setting unit 560 may obtain the minimum number of lighting colors (three lighting colors and two lighting colors) in which the separation degree exceeds the threshold for each of the plurality of inspection tools and the lighting color types (R, G, B; and R, IR1), and decide the logical sum (R, G, B, IR1) of the obtained lighting color types as the combination of recommended lighting colors.

The storage device 520 stores spectral image data 521 which is data of the spectral image acquired by the camera 4, gray image data 522 which is data of the gray image generated by the MSI processing unit 511, and the setting information 523 holding the various control parameters. In addition, the storage device 520 also stores various types of setting data, a program code for generating the user interface, and the like. The storage device 520 may also store and hold the inspection image generated from the gray image and the like.

Figure 16:
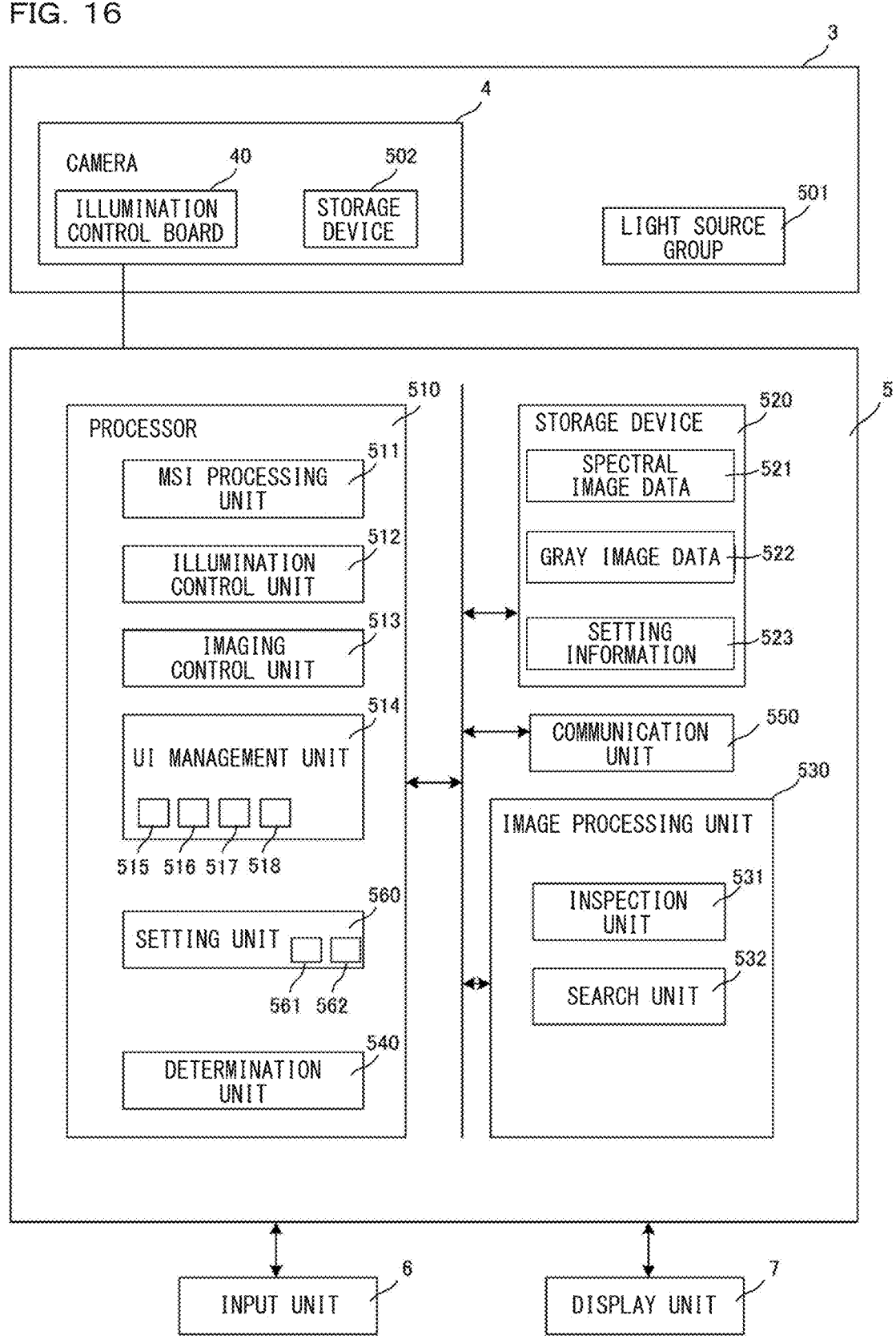
FIG. 16 is a diagram illustrating functions of an image processing system.
Figure 17:
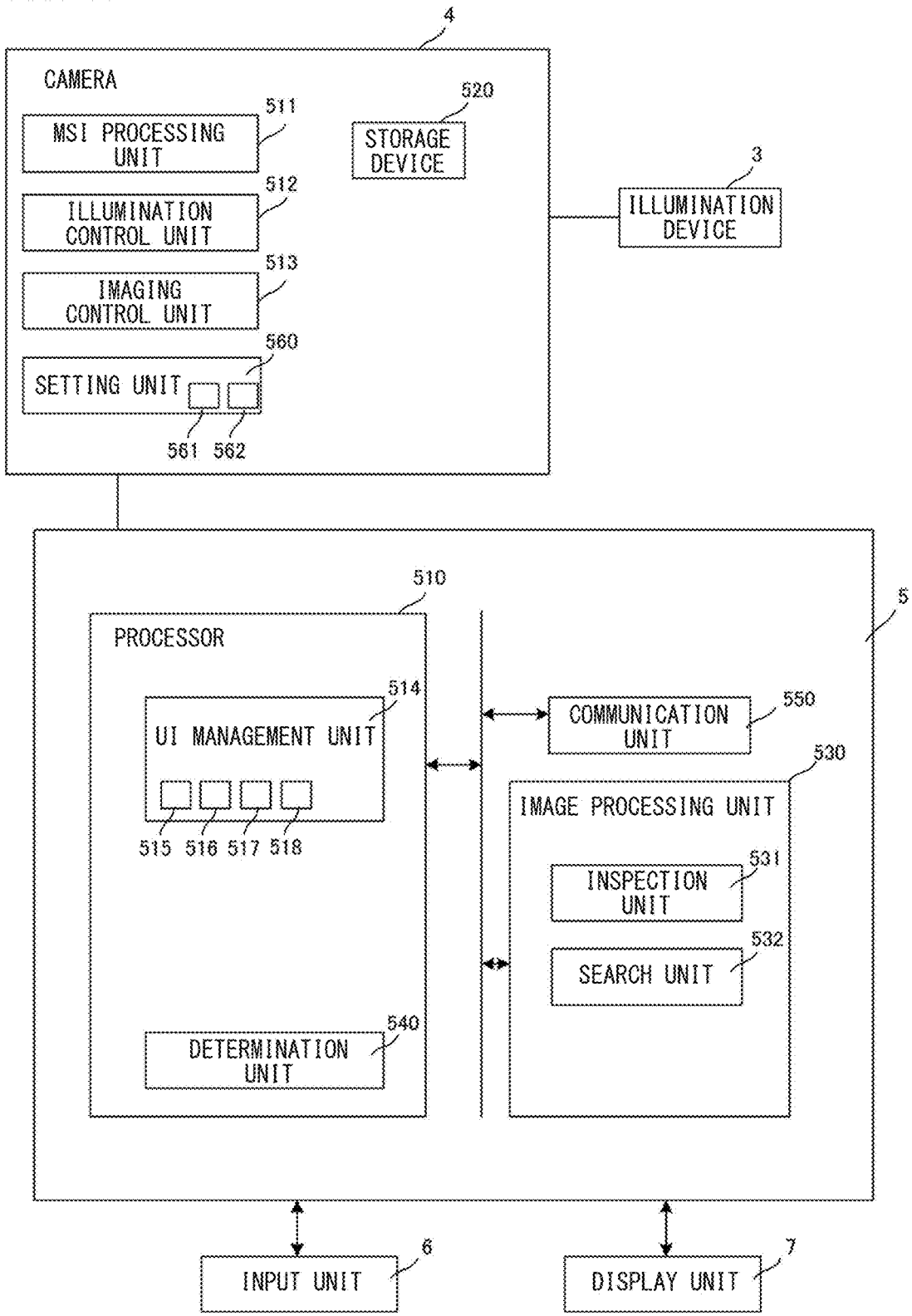
FIG. 17 is a diagram illustrating functions of an image processing system.
Figure 18:
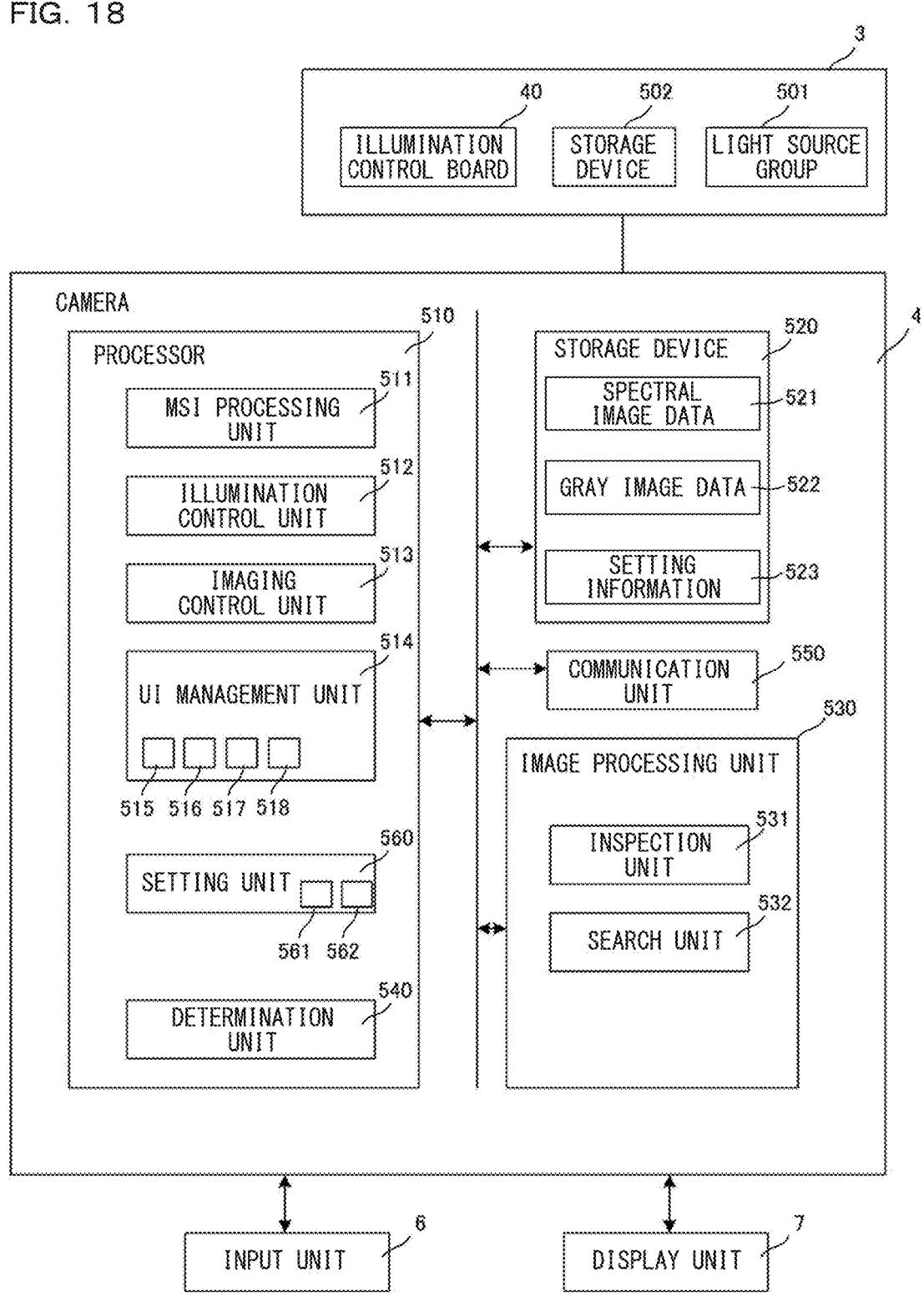
FIG. 18 is a diagram illustrating functions of an image processing system.

FIGS. 16 to 18 are diagrams illustrating other configuration examples of the image processing device of the present invention. FIG. 16 is the diagram illustrating an example in which the illumination device 3 and the camera 4 are integrated, and the illumination control board 40 configured to control the illumination device 3 is provided in the camera 4. Since the illumination device 3 and the camera 4 are integrally provided in this configuration, it is not necessary to perform positioning at the time of installing the illumination device 3 and the camera 4. In addition, the illumination control board 40 configured to control the light source group 501 and the storage device 502 are unnecessary on the illumination device 3 side, and the general-purpose illumination device 3 that does not include the illumination control board 40 and the storage device 502 can also be used. The user can remove the illumination device 3 connected to the camera 4 and replace the illumination device 3 with another type of illumination device. For example, it is possible to appropriately select other types of illumination devices, such as a ring illumination that emits only white light, instead of the illumination device 3 used for the multi-spectral imaging in the present invention. It is preferable that the camera 4 recognize the type of the connected illumination device 3 and reflect the type on the setting user interface. Accordingly, the user can perform the illumination setting on the user interface corresponding to an item that can be set in the connected illumination device 3. A method in which the illumination device 3 stores illumination type information and the camera 4 refers to the information is conceivable as a method of recognition. In addition, the illumination control unit 512 and the imaging control unit 513 included in the image processing device 5 may be provided inside the camera 4, and control of an imaging and illumination system may be executed independently from the image processing device 5.

FIG. 17 illustrates the configuration example in which some functions of the image processing device 5 are provided on the camera 4 side. The camera 4 includes the storage device 520 that stores the spectral image data 521, the gray image data 522, and the setting information 523, and the MSI processing unit 511 executes the process of generating the gray image data 522 from the spectral image data 521 inside the camera 4. The illumination device 3 is controlled by the illumination control unit 512 of the camera 4. At the time of inspection setting, the camera 4 transmits the spectral image data 521 captured at each wavelength and the gray image data 522 generated by the MSI processing unit 511 to the image processing device 5. At the time of setting, the image processing device 5 acquires the spectral image data 521 from the camera 4 and displays the acquired data on the display unit 7, so that the user can confirm the illumination intensity of each wavelength and whether the spectral image data 521 of each wavelength is necessary for inspection. On the other hand, at the time of inspection operation, only the gray image data 522 to be inspected may be transmitted to the image processing device 5 without transmitting the spectral image data 521 from the camera 4 to the image processing device 5. As the camera 4 is caused to have some functions of the image processing device 5 in this manner, a communication load between the camera 4 and the image processing device 5 is reduced, and the speed of processing increases due to distributed processing.

FIG. 18 is the configuration example in which all functions of the image processing device 5 are incorporated in the camera 4. It is sufficient for the user to install only the camera 4 and the illumination device 3, and thus, little time and effort is required at the time of installation. For example, this configuration may be advantageous when the camera 4 is allowed to have a large size and advanced image processing is unnecessary.

<Multi-Spectral Imaging>

In the multi-spectral imaging, the workpiece 2 is irradiated sequentially with illumination beams having different wavelengths (lighting colors) one by one, and an image for each lighting color is acquired. For example, eight images (spectral images) are acquired in the case of irradiation with illumination beams of eight types of lighting colors. When there are four illumination blocks, the four illumination blocks are turned on at the same time. That is, since the four LEDs 33 of the same lighting color are simultaneously turned on, the workpiece 2 is irradiated with the illumination beams of the same lighting color from four directions. For example, the eight types of lighting colors are light colors having eight types of narrow-band wavelengths between an ultraviolet lighting color to a near-infrared lighting color. The narrow-band wavelength refers to a wavelength narrower than a width of a wavelength (wide-band wavelength) of light emitted by the white LED. For example, a wavelength width of light emitted by a blue LED is much narrower than the wavelength width of the light emitted by the white LED, and thus, the wavelength of the light emitted by the blue LED is the narrow-band wavelength. In the image inspection, there may be image inspection that does not require all of the eight spectral images. In this case, the workpiece 2 is irradiated with only an illumination beam of a necessary lighting color. In general, it is unlikely that the eight images are directly used for image inspection, one gray image is created from the eight images (color gray-scale conversion), and this gray image (color gray-scale image) is used for the image inspection. The color gray-scale conversion is sometimes called color-gray conversion. For example, binarization processing is executed on the color gray-scale image, edge detection processing is executed, or blob processing is executed so that whether a position, a size (a length or area) and a color of a characteristic (for example, a pin) in the workpiece 2 fall within tolerance ranges, respectively, are inspected.

Figure 6:
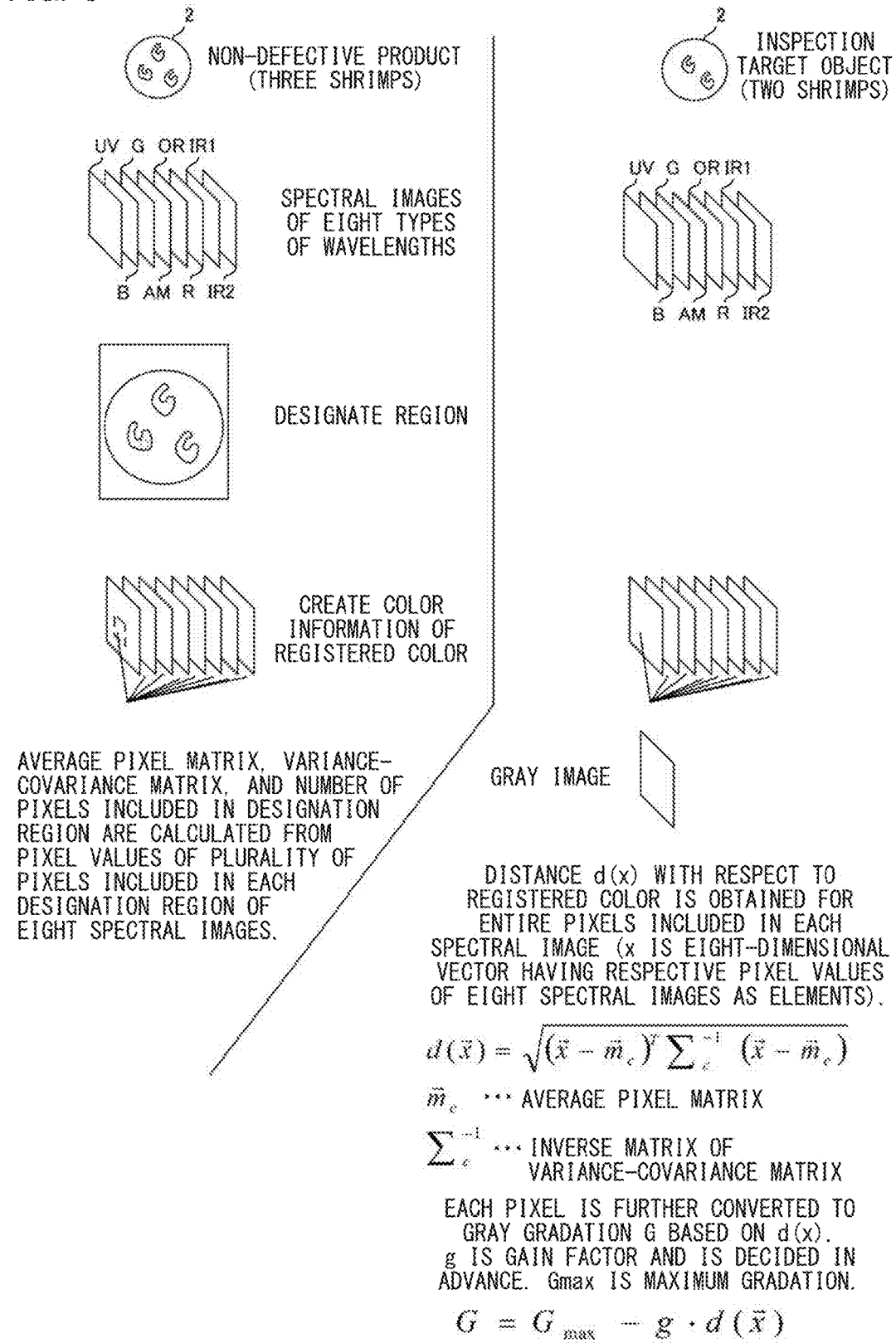
FIG. 6 is a view illustrating a principle of color gray-scale conversion in multi-spectral imaging.

An example of the color gray-scale conversion will be described with reference to FIG. 6. When creating the gray image of the workpiece 2 which is the inspection target object, a registered color of a non-defective product (model) is required. This is because the gray image is created by converting the eight spectral images using color information of the registered color as a reference.

First, in a setting mode, the color information of the registered color is extracted from an image region (designation region) designated by the user in the eight spectral images acquired from the non-defective product. For example, when the non-defective product is an instant food (for example, Chinese noodle) and the number of certain ingredients (for example, shrimps) is counted by image inspection, the user displays an image of the non-defective product and designates a rectangular designation region including the ingredient in the non-defective product image, and the color information of the registered color is extracted from pixels included in the designation region. The color information of the registered color includes an average pixel matrix, a variance-covariance matrix, and the number of the pixels included in the designation region. The color information may be extracted by a so-called dropper tool. An UI of the dropper tool may be implemented on the region designation unit 516.

Next, eight spectral images are acquired for the workpiece 2 as the inspection target object in the inspection mode. A distance d(x) with respect to the registered color is obtained for all pixels included in each spectral image (x is an eight-dimensional vector having the respective pixel values of the eight spectral images as elements). Further, a product is obtained by multiplying the distance d(x) by a predetermined gain g, an offset a is added if necessary, and a difference G obtained by subtracting the product from a maximum gradation Gmax that each pixel can take becomes a gray gradation of a pixel x of interest. This is expressed as G=Gmax−(g·d(x)+a).

When there are a plurality of registered colors, a plurality of gray images may be created using each registered color as a reference, or a single gray image may be created.

<Lighting Color Selection>

A wavelength (lighting color) required in image inspection depends on the workpiece 2. More specifically, the required lighting color depends on which characteristic portion of the surface of the workpiece 2 is to be inspected. Therefore, it is desirable that the lighting color be selected such that a characteristic portion to be inspected in an image of the workpiece 2 is appropriately separated from a surrounding portion thereof. In addition, as the number of lighting colors increases, it is easier to obtain an inspection image in which the characteristic portion can be separated from the surrounding portion, but the time that can be allocated to image inspection depends on the user. In addition, it takes more time to acquire the image and process the image as the number of lighting colors increases. Accordingly, an upper limit of the number of lighting colors is set such that an image inspection time becomes equal to or less than an allocable time. Accordingly, a combination of wavelengths suitable for the image inspection of the workpiece 2 is decided so as not to exceed the upper limit of the number of lighting colors.

User Interface

Figure 7:
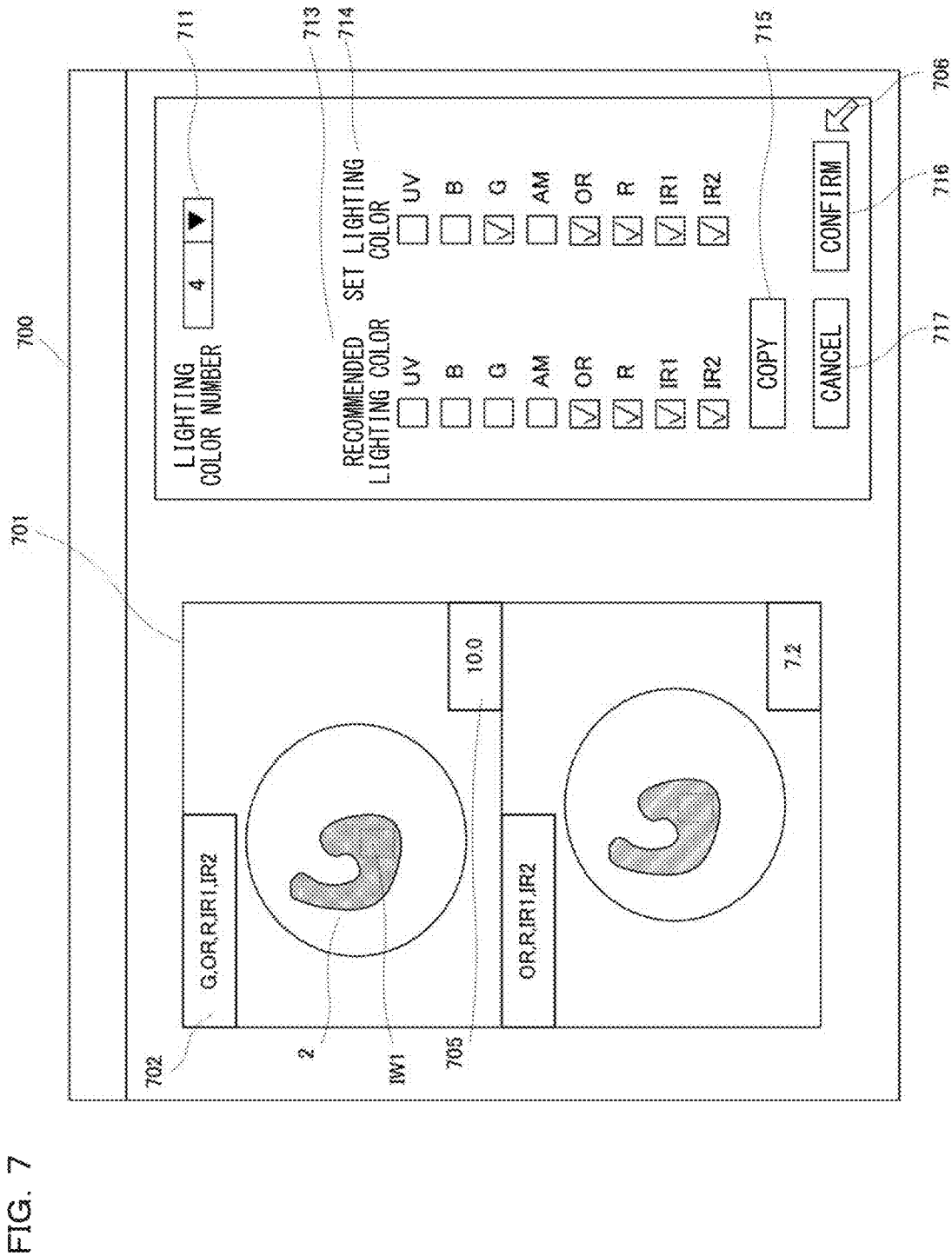
FIG. 7 is a view illustrating a UI that assists selection of a lighting color.
Figure 8:
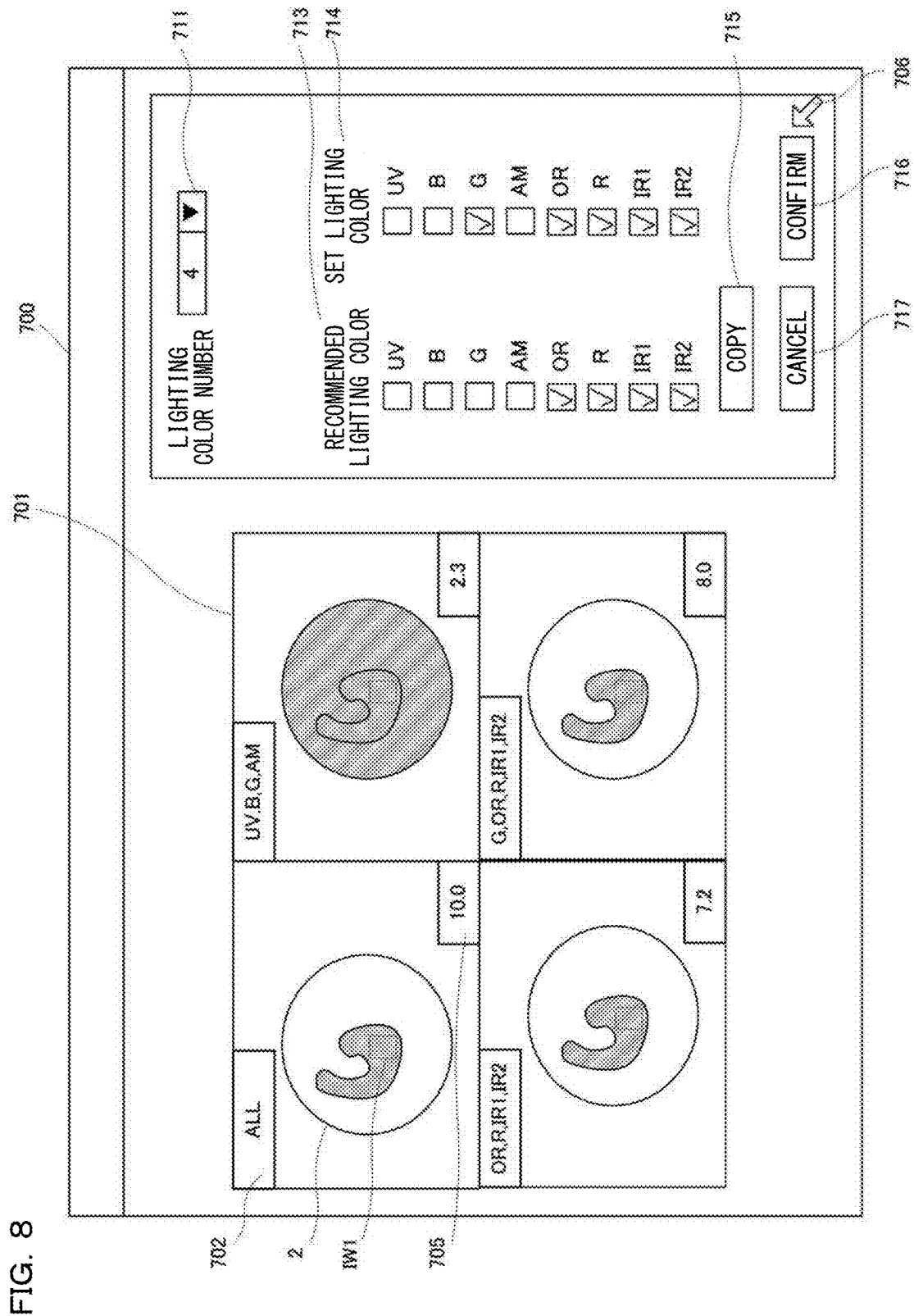
FIG. 8 is a view illustrating a UI that assists selection of a lighting color.
Figure 9:
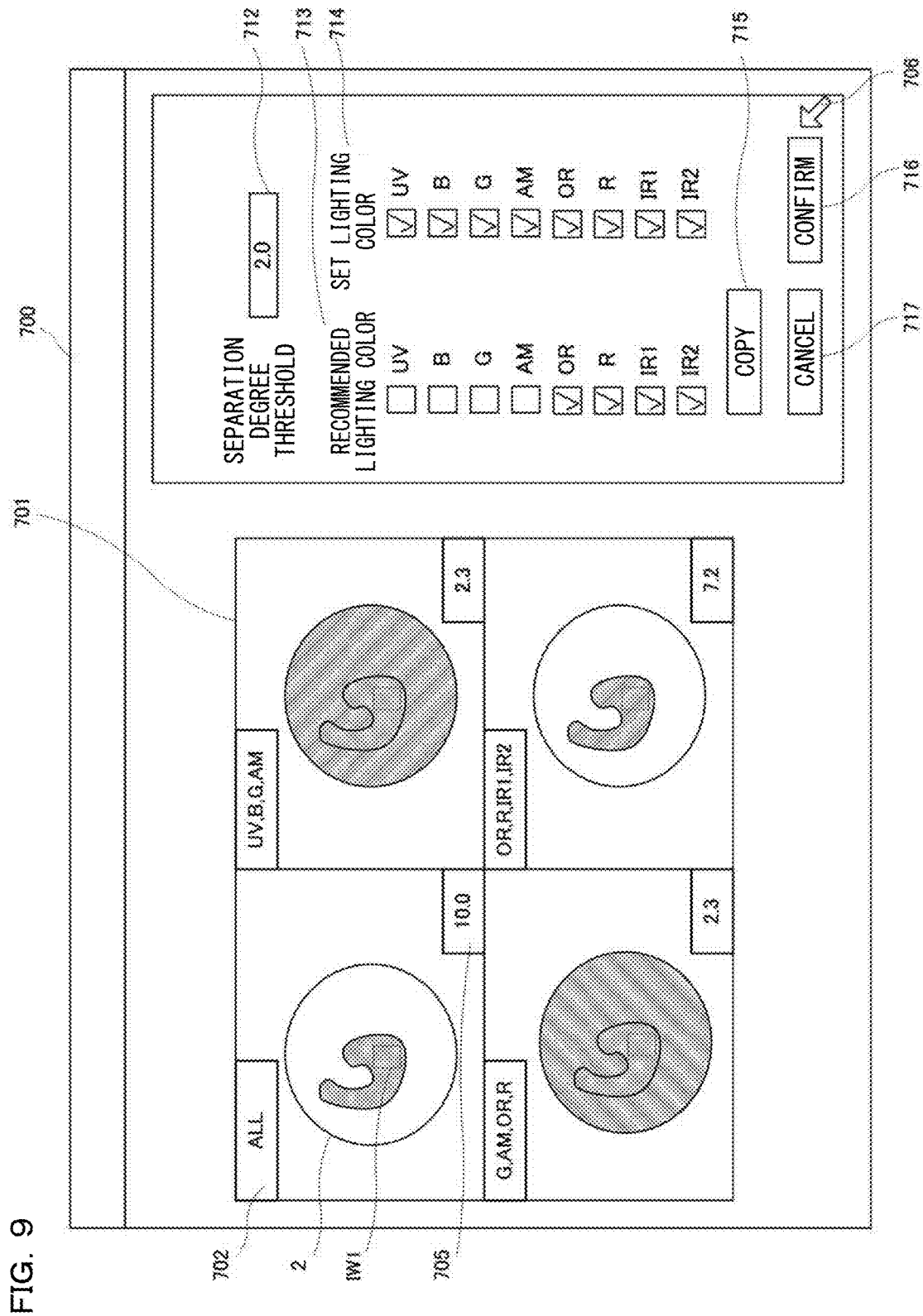
FIG. 9 is a view illustrating a UI that assists selection of a lighting color.

FIGS. 7, 8, and 9 illustrate user interfaces for lighting color selection which are displayed on the display unit 7 by the UI management unit 514. A UI 700 is a UI that assists the user in selecting a wavelength of an illumination beam required to illuminate the workpiece 2. In particular, a combinations of recommended lighting colors and set lighting colors customized by adding or removing a lighting color to or from the combination of recommended lighting colors by the user are displayed in the UI 700 in FIG. 7.

One or more gray images created from a plurality of spectral images, acquired by capturing the image of the workpiece 2, by the MSI processing unit 511 are displayed in an image display region 701. According to FIG. 7, a gray image obtained by customizing the lighting colors by the user is displayed on the upper side, and a gray image generated by the combination of recommended lighting colors is displayed on the lower side. The image displayed on the upper side and the image displayed on the lower side may be reversed. The gray image is updated every time the user adds or deletes a lighting color. According to FIG. 8, a different UI 700 is illustrated. In this example, a gray image acquired by using all the eight lighting colors, and two gray images each of which has the separation degree within the second rank from the top among combinations of lighting colors that is equal to or less than a designated lighting color number are displayed. Further, a gray image acquired by customizing the lighting colors by the user is also displayed. That is, the gray image created from eight spectral images (wavelength images), the gray image created from four spectral images, and the gray image created from five spectral images are displayed. The eight lighting colors are all of the lighting colors provided in the illumination device. In addition, the five lighting colors are the lighting colors selected by a set lighting color display unit 714 configured to select the set lighting color. Each gray image includes a lighting color display unit 702 to display a used lighting color and a separation degree display unit 705 to display the separation degree calculated by the calculation unit 561. IW1 indicates an inspection region assigned to a part of the workpiece 2. An inspection region 704 may also be used as a designation region including a color (registered colors such as the foreground color and the background color) that the user desires to extract. The MSI processing unit 511 may create a false color image by applying color to the gray image in a pseudo manner, and display the false color image on the image display region 701 instead of the gray image. This is because it is easier for the user to confirm that the color that is desirably extracted is separated and extracted from the other colors in the false color image colored in a pseudo manner than in the simple gray-scale image. The MSI processing unit 511 may directly create a false color image (RGB image) from a group of the eight spectral images according to the combination of the designated lighting color number. When a total lighting color number N is eight and a designated number M is four, the number of the false color images is 8C4 (that is, 70).

A pull-down menu 711 illustrated in FIGS. 7 and 8 functions as a lighting color number selection unit configured to receive, from the user, selection of an upper limit value (the maximum lighting-possible number M) of the number of lighting colors of the illumination beams with which the workpiece 2 is irradiated. A text box 712 illustrated in FIG. 9 functions as a separation degree threshold input unit that receives an input of a threshold to be compared with a calculated separation degree by the user. A method of using the number of lighting colors as a reference and a method of using a threshold as a reference are conceivable as a method of deciding a pattern of recommended lighting colors. The former method is a method of obtaining evaluation values (separation degrees), respectively, for combinations of lighting colors equal to or less than the number of lighting colors designated by the user, and deciding a combination in which the maximum separation degree has been obtained as a recommended combination. The latter method is a method of deciding a combination having the smallest number of lighting colors as the recommended combination among the combinations of lighting colors in which the separation degree equal to or greater than the threshold designated by the user has been obtained. When these two methods are implemented on the image processing device, the UI management unit 514 may provide a UI for selection of any one of the methods to the user.

A recommended lighting color display unit 713 is a check box which indicates the combination of lighting colors determined to be the recommended lighting colors based on the separation degree. However, the recommended lighting color display unit 713 may be inoperable by the user. In this manner, the combination of recommended lighting colors may become clear. For example, the setting unit 560 may display a combination of lighting colors in which the maximum separation degree has been obtained among the combinations of lighting colors based on the designated lighting color number on the recommended lighting color display unit 713. The combinations of the lighting colors in which the maximum separation degree has been obtained among the combinations of lighting colors based on the designated lighting color number is decided by the decision unit 562. The decision unit 562 decides the combination (lighting pattern) of lighting colors in which the separation degree obtained by the calculation unit 561 is the maximum as the combination of recommended lighting colors. The UI management unit 514 displays the image having the maximum separation degree, the combination of lighting colors, and the separation degree in the image display region 701. When the decision unit 562 notifies the UI management unit 514 of the combination of lighting colors having the maximum separation degree, the UI management unit 514 displays the combination of lighting colors having the maximum separation degree in the recommended lighting color display unit 713.

In addition, the setting unit 560 may display, on the set lighting color display unit 714, a combination of lighting colors which have been used to acquire a gray image clicked by a pointer 706 among three gray images based on the designated lighting color number. The set lighting color display unit 714 is, for example, a check box. When a confirm button 716 is operated, a combination of lighting colors checked in the set lighting color display unit 714 at that time is set in the MSI processing unit 511. The combination of lighting colors displayed by the set lighting color display unit 714 is a combination of lighting colors of illumination beams used to acquire the gray image displayed at the lower right among the four images. The gray image is updated based on the spectral image acquired by the lighting color checked in the set lighting color display unit 714 every time a lighting color is added or deleted in the set lighting color display unit 714.

A gray image (before customization) based on the recommended lighting color and a gray image (after customization) based on the set lighting color are displayed in FIG. 7, but either of these images may be displayed alone while being switched. In FIG. 8, the gray image based on the recommended lighting color and the gray image based on the set lighting color are displayed in addition to the gray image based on all the lighting colors. A plurality of gray images based on a plurality of combinations of set lighting colors may be displayed by preparing a plurality of the set lighting color display units 714. In addition, a plurality of gray images based on a plurality of combinations of recommended lighting colors and a plurality of gray images based on a plurality of combinations of set lighting colors may be displayed.

A copy button 715 is a button to copy a combination of lighting colors displayed on the recommended lighting color display unit 713 to a combination of lighting colors displayed on the set lighting color display unit 714. When a confirm button 716 is operated, the UI management unit 514 writes the combination of lighting colors (combination of lighting colors displayed on the set lighting color display unit 714) set by the setting unit 560 to the setting information 523. When a cancel button 717 is operated, the UI management unit 514 cancels the combination setting of lighting colors and returns to the previous setting.

Figure 10:
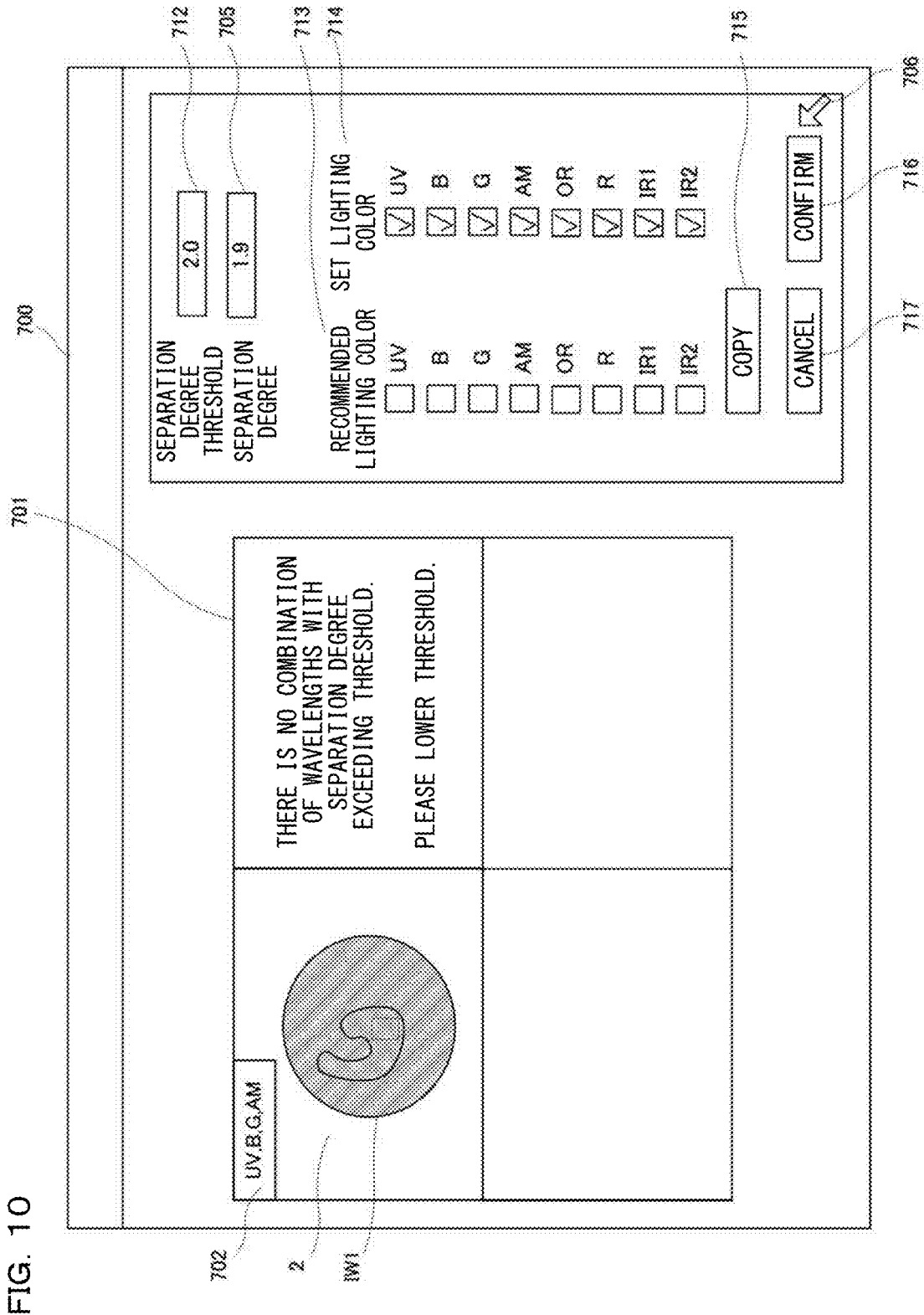
FIG. 10 is a view illustrating a UI that assists selection of a lighting color.

FIG. 10 illustrates a UI that the UI management unit 514 displays on the display unit 7 when not a single combination of lighting colors having a separation degree exceeding a separation degree threshold set by the user is found. In this example, the UI management unit 514 may display, on the display unit 7, a message indicating that no combination of lighting colors having the separation degree exceeding the threshold has been found. In addition, the UI management unit 514 may display a message suggesting to lower the separation degree threshold on the display unit 7. Accordingly, the user lowers the separation degree threshold. For example, if there is room for inspection accuracy, the separation degree threshold is decreased.

When there is no lighting pattern having the separation degree exceeding the separation degree threshold, the decision unit 562 may decide the combination of lighting colors having the maximum separation degree among a plurality of calculated separation degrees as the combination of recommended lighting colors. The UI management unit 514 may display the text box 712 indicating the separation degree threshold and a text box (the separation degree display unit 705) indicating the maximum separation degree thus calculated side by side. Accordingly, it may be easy for the user to confirm how far the calculated separation degree is from the separation degree threshold.

Figure 11:
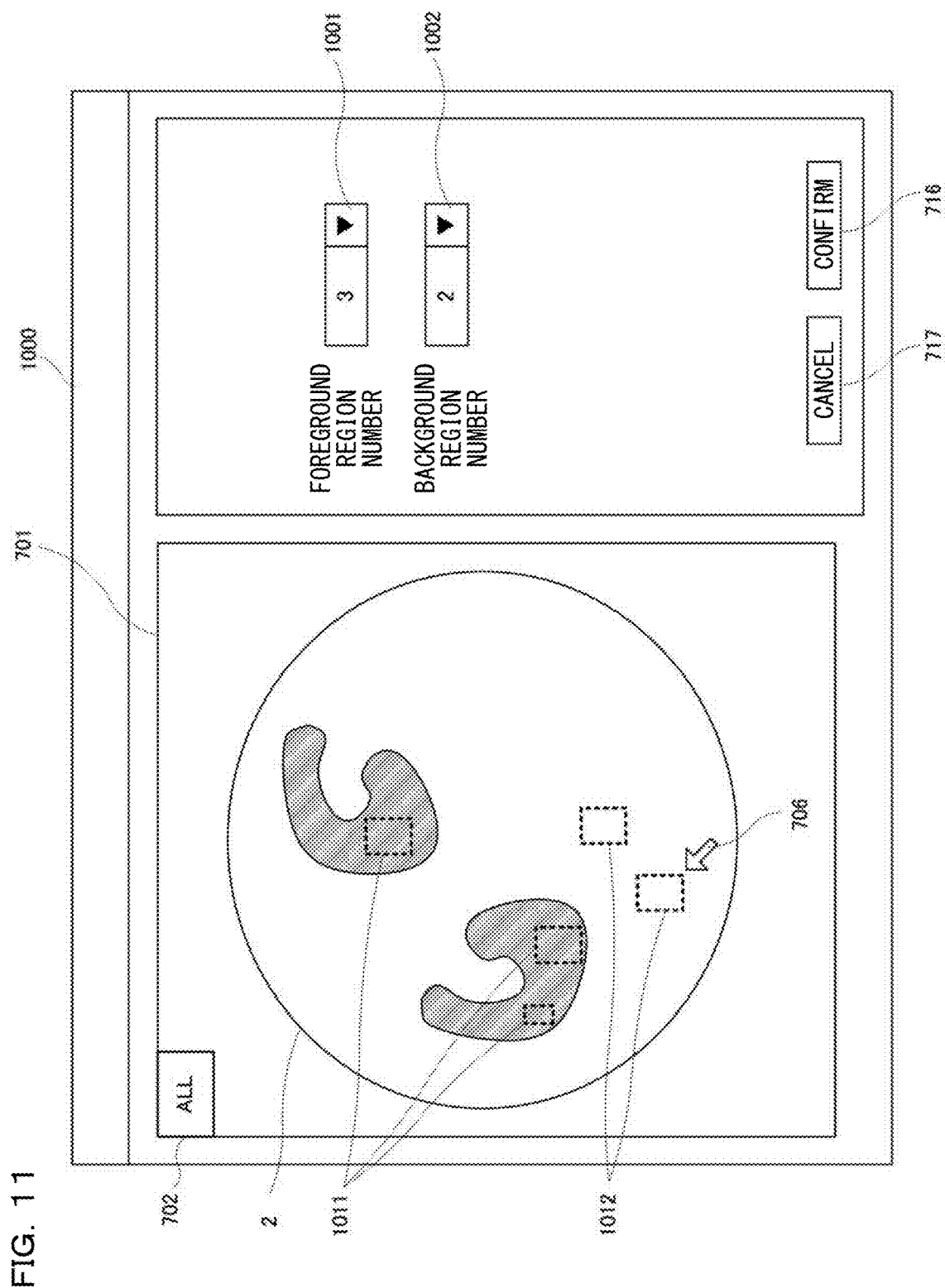
FIG. 11 is a view illustrating a UI that assists selection of a foreground region and a background region.

FIG. 11 illustrates a user interface configured to set the foreground region and the background region. As described above, the separation degree is the distance between the color information (foreground color) of a foreground region 1011 and the color information (background color) that is extracted from a background region 1012 and needs to be distinguished from the foreground color. This distance is the distance between the pieces of the color information in the color space. In general, the foreground region is a region including characteristics of the inspection target object in the image of the workpiece 2. The background region is a region including the background color that is desirably distinguished from the foreground color. In this manner, both the foreground color and the background color are the registered colors registered by the user. The background color, however, may be decided by the image processing device using the color information of the foreground color.

In general, as the distance between a distribution of the foreground color (extracted color) and a distribution of the background color (distinguished color) in the color space increases, an inspection image improving image inspection accuracy is obtained. The number of each of the foreground region and the background region may be one or more. A region setting UI 1000 includes a pull-down menu 1001 configured to set the number of foreground regions and a pull-down menu 1002 configured to set the number of background regions. The region designation unit 516 of the UI management unit 514 displays frames of the foreground regions 1011 corresponding to the number designated by the pull-down menu 1001 and frames of the background regions 1012 corresponding to the number designated by the pull-down menu 1002 to be superimposed on the image of the workpiece 2 displayed in the image display region 701.

Although the plurality of foreground regions and the plurality of background regions can be designated here, each one of these regions can be also designated. In addition, the region designation unit 516 may receive designation of the foreground color and the background color by a so-called dropper. Since a certain point is designated by the dropper, the region designation unit 516 may decide color information of registered colors based on a color of the designated point and a color similar to that color.

The image of the workpiece 2 may be a false color image (RGB image) created by using all of the eight lighting colors.

The region designation unit 516 may adjust a position and a size of the frame designating the foreground region or adjust a position and a size of the frame designating the background region in accordance with the operation of the pointer 706.

As described above, the region designation unit 516 may automatically register the background color based on the color information of the foreground color. For example, the region designation unit 516 may cluster the image of the workpiece 2 into a plurality of color clusters, calculate a distance between the foreground color and each color cluster, and register a color cluster whose calculated distance is equal to or larger than a threshold as the background color. The number of the color clusters generated by clustering is designated in advance by the user. Accordingly, the user can save the time and effort for designating the background region and the background color. When the user is allowed to designate the background region as well, the combination of recommended lighting colors which enables more accurate acquisition of the extracted color is decided.

Concept of Separation Degree

Figure 12:
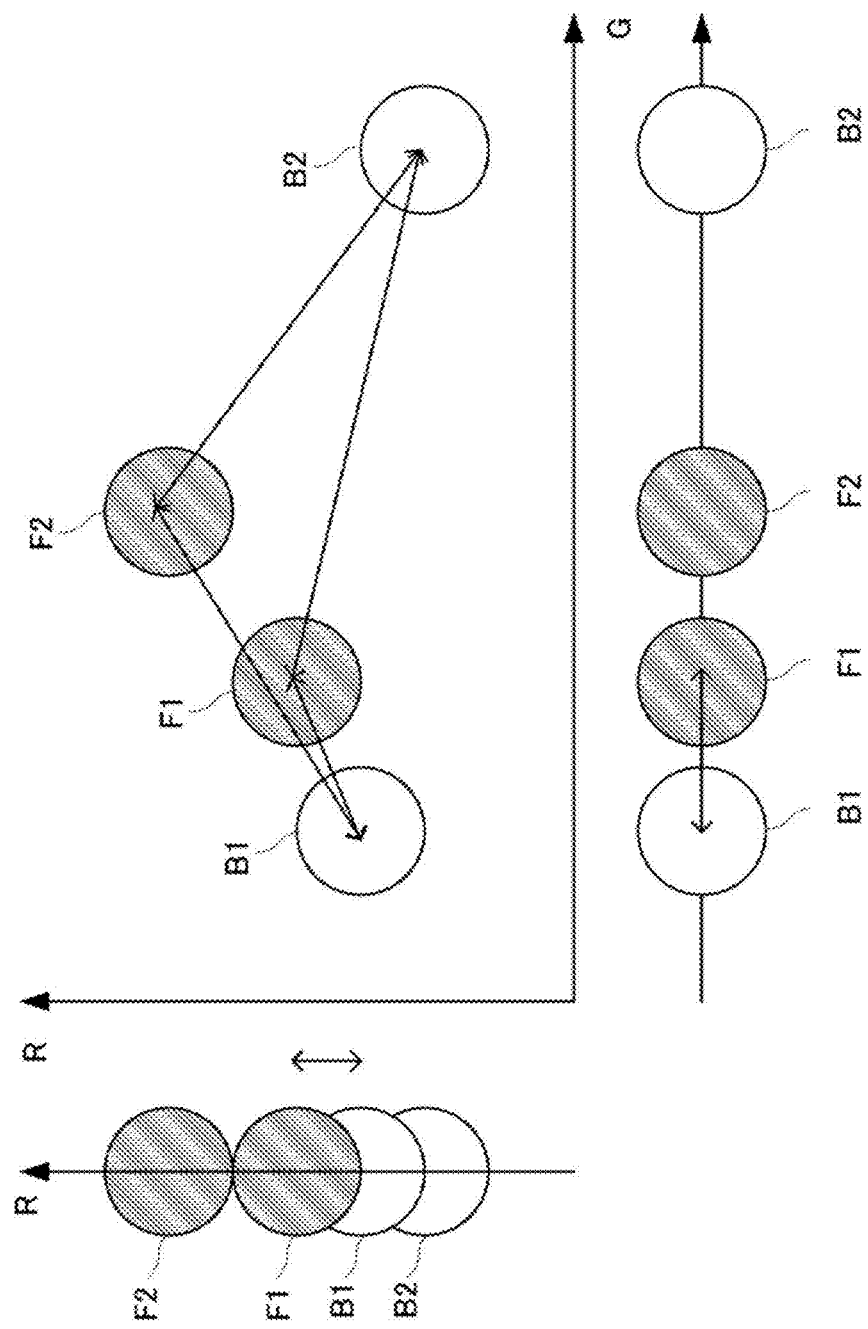
FIG. 12 is a view for describing a concept of a separation degree.

FIG. 12 is a view for describing a concept of the separation degree. This example shows which one of lighting colors of R and G can be reduced. A first foreground color F1, a second foreground color F2, a first background color B1, and a second background color B2 are set on the image of the workpiece 2. A circle in FIG. 12 indicates a distribution (color information) of each registered color. In this example, each distribution is circular and has the same size in order to simplify the description.

The calculation unit 561 calculates each separation degree for all combinations of the foreground colors and the background colors (four combinations in this example). First, the calculation unit 561 obtains a separation degree between color information of the first foreground color F1 and color information of the first background color B1, a separation degree between the color information of the first foreground color F1 and color information of the second background color B2, a separation degree between color information of the second foreground color F2 and the color information of the first background color B1, and a separation degree between the color information of the second foreground color F2 and the color information of the second background color B2, based on a spectral image of R and a spectral image of G. As illustrated in FIG. 12, it can be understood that all these four separation degrees become sufficient values if the lighting colors of R and G are used. A bidirectional arrow indicates a magnitude of the separation degree.

Meanwhile, if only the lighting color of R is used without using the lighting color of G, three separation degrees among the four separation degrees become sufficient values, but the minimum separation degree among the four separation degrees becomes an insufficient value. That is, the separation degree between the color information of the first foreground color F1 and the color information of the first background color B1 becomes too small, so that it is difficult to sufficiently separate the color information of the first foreground color F1 from the color information of the first background color B1.

On the other hand, if only the lighting color of G is used without using the lighting color of R, the separation degree between the color information of the first foreground color F1 and the color information of the first background color B1 becomes the minimum separation degree among the four separation degrees, but it is possible to separate the color information of the first foreground color F1 and the color information of the first background color B1. Accordingly, the decision unit 562 decides a lighting pattern that uses the lighting color of G without using the lighting color of R as the combination of recommended lighting colors.

The separation degree may be a distance (Euclidean distance in the color space) between an average color in the distribution of the foreground color and an average color in the distribution of the background color, or may be a Fisher score.

The color information of the first foreground color F1 and the color information of the second foreground color F2 may be grouped as color information of a first group. In addition, the color information of the first background color B1 and the color information of the second background color B2 may be grouped as color information of a second group. The calculation unit 561 may calculate a distance between a distribution of the color information of the first group and a distribution of the color information of the second group as an inter-group distance (intergroup separation degree). In addition, the first group may be a group including a plurality of registered colors, and the second group may be a group including a plurality of different registered colors. It is assumed that the registered color is selected in advance from the color image of the workpiece 2 by the user.

Flowchart

Figure 13:
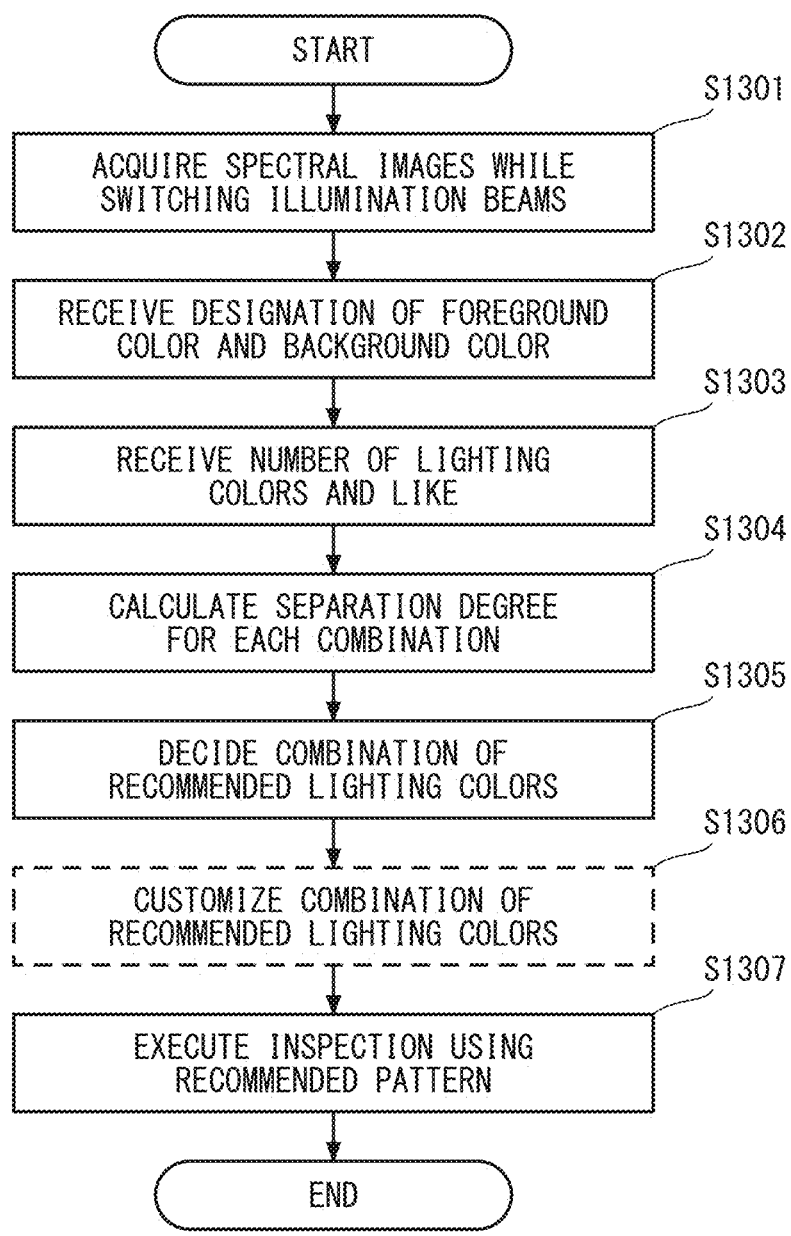
FIG. 13 is a flowchart illustrating image inspection including a process of deciding a combination of recommended lighting colors.

FIG. 13 is a flowchart illustrating the image inspection including the process of deciding a combination of recommended lighting colors. S1301 and S1302 correspond to a phase of acquiring color information, and S1303 to S1307 correspond to a phase of deciding the combination of recommended lighting colors.

In S1303, the processor 510 (the MSI processing unit 511) acquires spectral images while switching illumination beams. Here, the spectral images are acquired for all lighting colors. For example, the MSI processing unit 511 instructs the illumination control unit 512 to irradiate a setting target object individually with illumination beams of N lighting colors in a predetermined order. The illumination control unit 512 instructs the illumination control board 40 to irradiate the setting target object individually with the illumination beams of the N lighting colors in the predetermined order according to the instruction from the MSI processing unit 511. The illumination control board 40 selects one of the N lighting colors by turning on one of the N switches 43 according to the instruction from the illumination control unit 512, and turns on the LED 33 capable of emitting the illumination beam of the selected lighting color. When receiving a signal indicating that the LED 33 of a first lighting color has been turned on from the illumination control unit 512, the MSI processing unit 511 instructs the imaging control unit 513 to capture the image of the setting target object. The imaging control unit 513 controls the camera 4 to acquire a spectral image for the first lighting color and writes the acquired spectral image as the spectral image data 521 to the storage device 520. When receiving a signal, which indicates that acquisition of the spectral image of the first lighting color has been completed, from the imaging control unit 513, the MSI processing unit 511 instructs the illumination control board 40 to turn off the LED 33 of the first lighting color and turn on the LED 33 of a next lighting color via the illumination control unit 512. The illumination control board 40 turns on the LED 33 of the next lighting color by switching the switch 43 corresponding to the first lighting color to off and switching the switch 43 corresponding to the next lighting color to on. Similarly, the imaging control unit 513 acquires a spectral image of the next lighting color. Such lighting and imaging are executed for all the N lighting colors, and finally, N spectral images are acquired.

In S1302, the processor 510 (the UI management unit 514) receives designation of the foreground color and the background color. Regarding the background color, the UI management unit 514 may decide the background color based on the foreground color in order to reduce the burden on the user.

In S1303, the processor 510 (UI management unit 514) receives the number of lighting colors or the separation degree threshold. For example, the UI management unit 514 displays the UI 700 as illustrated in FIGS. 7 and 8 on the display unit 7, receives the number of lighting colors, and saves the number of lighting colors in the setting information 523. The UI management unit 514 displays the UI 700 as illustrated in FIG. 9 and the like on the display unit 7, receives the separation degree threshold, and stores the separation degree threshold in the setting information 523.

In S1304, the processor 510 (the setting unit 560) calculates the separation degree for each combination of lighting colors. The setting unit 560 decides a combination of lighting colors based on the total number of lighting colors and the number of lighting colors designated by the user. If the total number of lighting colors is N and the number of designated lighting colors is M, the number C of lighting color combinations is calculated by N!/(M!(N−M)!). "!" is a factorial operator. In the case where the four lighting colors are selected from the eight lighting colors of UV to IR2, 70 combinations in total including a combination of UV, R, IR1, and IR2 and the like are decided by the setting unit 560. The decided combination is saved in the setting information 523. In addition, when the designated lighting color number is input as the upper-limit lighting color number, combinations including (M−1) lighting colors to combinations including one lighting color may be further decided. If M=4, the setting unit 560 determines combinations of three lighting colors among the eight lighting colors, combinations of two lighting colors among the eight lighting colors, and combinations of one lighting color among eight lighting colors are decided. The calculation unit 561 calculates the separation degree between the foreground color and the background color for the spectral image corresponding to each combination of lighting colors.

In S1305, the processor 510 (the decision unit 562) decides the combination of recommended lighting colors based on the calculated separation degree. For example, the decision unit 562 may decide the combination having the maximum separation degree among the combinations decided based on the designated lighting color number as the combination of recommended lighting colors. In addition, the separation degree threshold may be designated instead of the number of lighting colors in some cases. In this case, the decision unit 562 may decide the lighting pattern having the separation degree equal to or higher than the separation degree threshold and the smallest number of lighting colors among all the combinations of lighting colors formed by all the lighting colors, as the combination of the recommended lighting colors. It is assumed that the arithmetic expression of the separation degree is stored in the storage device 520 in advance.

S1306 is an option. In S1306, the UI management unit 514 displays the combination of the recommended lighting colors on the display unit and receives addition or deletion (customization) of a lighting color with respect to the combination of recommended lighting colors. In this case, the calculation unit 561 calculates a separation degree for the customized combination of lighting colors, and displays the separation degree on the display unit. Finally, the combination confirmed by the user is used for image inspection.

Meanwhile, when the user instructs to execute the image inspection by applying a plurality of inspection tools for the inspection target object (the workpiece 2 conveyed by the line 1), the calculation unit 561 obtains a separation degree for each inspection tool. When the number of lighting colors is designated, the decision unit 562 may decide a combination of recommended lighting colors for each inspection tool, and decide a logical sum of the plurality of combinations of recommended lighting colors thus decided as a final combination of recommended lighting colors. For example, when UV, IR1, and IR2 are decided as a combination of recommended lighting colors for a flaw inspection tool, and UV, B, G are decided as a combination of recommended lighting colors for an area inspection tool, the decision unit 562 decides UV, B, G, IR1, IR2 as the final combination of recommended lighting colors.

Accordingly, five types of spectral images are acquired, but the MSI processing unit 511 creates an inspection image for each inspection tool from three types of spectral images corresponding to the combination of the recommended lighting colors thereof. For example, for the flaw inspection tool, the MSI processing unit 511 creates the inspection image for the flaw inspection from the spectral image of UV, the spectral image of IR1, and the spectral image of IR2. A reason why the separation degree differs for each inspection tool is that the position of the inspection region used to obtain the separation degree and the registered color are different for each inspection tool. That is, the characteristic to be inspected (a part of the surface of the workpiece 2) differs for each inspection tool. Of course, all the five types of spectral images may be used for each inspection tool.

On the other hand, when the separation degree threshold is designated, the decision unit 562 may decide a combination of lighting colors that allows separation degrees of all the inspection tools to be equal to or higher than the separation degree threshold as the combination of recommended lighting colors. In this case as well, the combination in which the separation degree is equal to or higher than the separation degree threshold and the number of lighting colors is the minimum is decided as the combination of recommended lighting colors.

In S1307, the processor 510 (determination unit 540) causes the inspection unit 531 to execute image inspection on the inspection image created by the MSI processing unit 511. As described above, the MSI processing unit 511 causes the illumination device 3 to illuminate illumination beams according to the combination of the recommended lighting colors to the inspection target object (the workpiece 2 conveyed on the line 1) and causes the camera 4 to acquire the spectral images of the workpiece 2. Further, the MSI processing unit 511 reads the spectral image acquired using the combination of recommended lighting colors from the storage device 520, creates the inspection image (a gray image, a binary image created from the gray image, and the like), and causes the storage device 520 to store the inspection image. The inspection unit 531 reads the inspection image from the storage device 520 and executes the image inspection using the inspection tool designated by the user. In the case of the flaw inspection tool, the area of a flaw is calculated. When the area of the flaw is within a tolerance (threshold), the determination unit 540 determines that the inspection target object as a passed product. In addition, the determination unit 540 determines the inspection target object as a rejected product if the area of the flaw exceeds the tolerance (threshold).

<Others>

Setting UI of Inspection Tool

Figure 14:
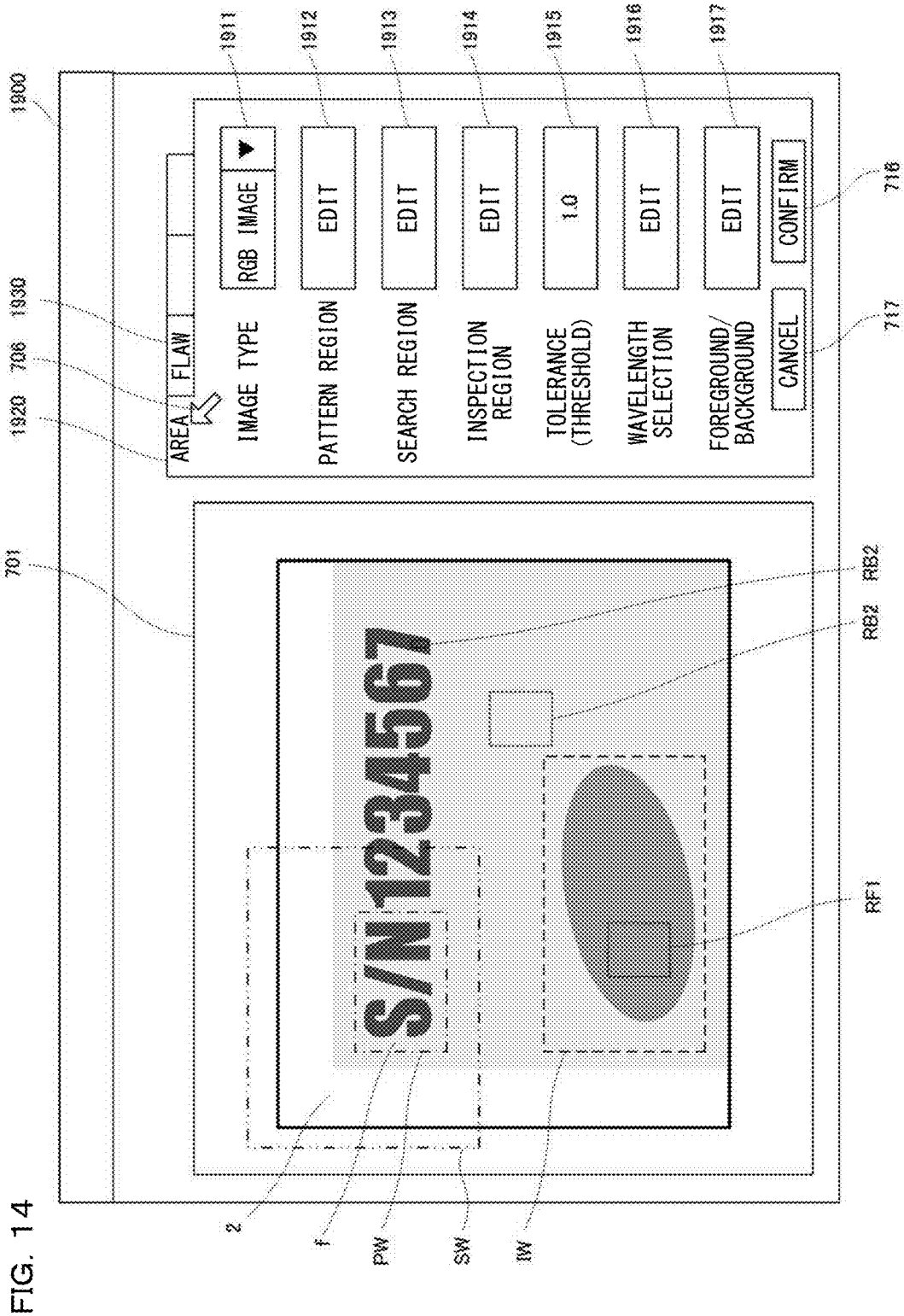
FIG. 14 is a view illustrating a UI that assists setting of an inspection tool.

FIG. 14 illustrates a setting UI 1900 for setting of parameters of the inspection tool. When a setting mode is selected by the user, the UI management unit 514 displays the setting UI 1900 on the display unit 7. A setting tab 1920 is a UI for setting of parameters relating to the area inspection tool. A setting tab 1930 is a UI for setting of parameters relating to the flaw inspection tool. In FIG. 14, the setting tab 1920 is selected by the pointer 706. An image type setting unit 1911 is a pull-down menu for selection of an image displayed in the image display region 701. In the pull-down menu, a gray image, an RGB image, and the like generated by capturing the image of the workpiece 2 are registered. In FIG. 14, the workpiece 2 is a card (membership card or the like) on which characters and patterns are printed. The image selection unit 515 of the UI management unit 514 reads the image selected by the image type setting unit 1911 from the storage device 520 and displays the read image in the image display region 701. An edit button 1912 is a button configured to edit a size and a position of a pattern region PW which is a region including a characteristic f to be subjected to pattern search by the search unit 532. The characteristic f surrounded by the pattern region PW is stored in the storage device 520 as a registration pattern. An edit button 1913 is a button configured to edit a size and a position of a range (search region SW) for searching the characteristic f. The region designation unit 516 adjusts the sizes and positions of the pattern region PW and the search region SW according to the user's operation and saves an adjustment result in the setting information 523. When executing image inspection for a plurality of workpieces 2, positions and angles of the respective workpieces 2 are not fixed in a plurality of images acquired by the camera 4. However, the characteristic f often falls within a certain region within each of the images. Thus, the search unit 532 obtains a position and an angle of a registration pattern by searching the registration pattern (characteristic f) within the search region SW. These position and angle are used to correct a position and an angle (position correction) of the inspection region IW. An edit button 1914 is a button configured to edit a size and the position of the inspection region IW. In this example, the inspection region IW is set so as to surround the pattern printed on the card. Accordingly, whether the area of the pattern falls within a tolerance is inspected. The region designation unit 516 adjusts the size and the position of the inspection region IW according to the user's operation and saves an adjustment result in the setting information 523. The inspection unit 531 calculates the area of the pattern in the inspection region IW. A tolerance input unit 1915 is a text box that receives an input of the tolerance (threshold) serving as a reference for determination on the area of the pattern by the determination unit 540. The confirm button 716 is a button configured to confirm settings relating to the inspection tool. The cancel button 717 is a button configured to cancel the current settings and return to immediately preceding settings or default settings. A lighting color selection edit button 1916 is a button configured to edit the combination of recommended lighting colors. An edit button 1917 is an edit button for the foreground region and the background region. In this example, a foreground region RF1 is set in a part of the pattern. In addition, a background region RB1 is set in a base portion of the card. Further, a background region RB2 is set on the characters of the card. The region designation unit 516 adjusts a size and a position of the foreground region RF1 according to the user's operation, adjusts sizes and positions of the background regions RB1 and RB2, and saves adjustment results in the setting information 523.

Figure 15:
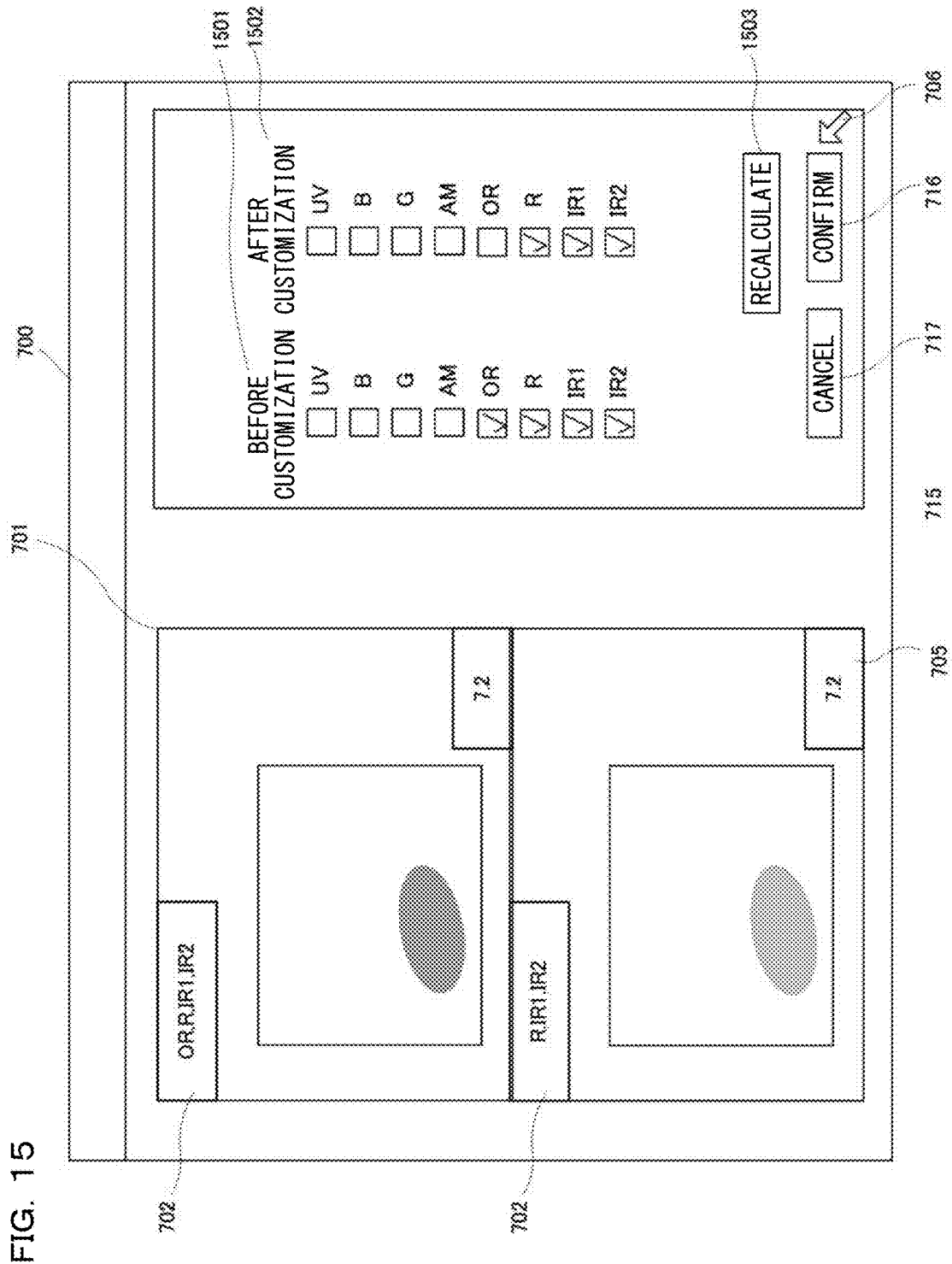
FIG. 15 is a view illustrating a UI that assists selection of a wavelength.

FIG. 15 illustrates another example of the UI 700 for customization of the combination of recommended lighting colors. A check box 1501 is an object indicating a combination of lighting colors before customization. The combination of lighting colors before customization indicates, for example, the combination of recommended lighting colors decided by the decision unit 562 or a combination of lighting colors set in the image processing device at this point in time. The check of the check box 1501 cannot be removed.

A check box 1502 is an object indicating a combination of lighting colors after customization. That is, the check box 1502 is an object indicating the lighting color finally designated by the user. When the UI 700 is first displayed, the check box 1502 indicates the combination of recommended lighting colors.

In this example, the combination of recommended lighting colors as the combination of lighting colors before customization corresponds to OR, R, IR1, and IR2. Two images are included in the image display region 701, and a gray image generated from spectral images corresponding to the combination of lighting colors before customization is displayed on the upper image.

As illustrated in FIG. 15, in the check box 1502 indicating the combination of lighting colors after customization, the user deletes the lighting colors of OR by removing the check of a check box of OR.

A recalculation button 1503 is a button for causing the calculation unit 561 to recalculate a separation degree based on spectral images corresponding to the combination of lighting colors after customization. That is, when the recalculation button 1503 is pressed, the UI management unit 514 instructs the calculation unit 561 to recalculate the separation degree based on the spectral images corresponding to the designated lighting colors (R, IR1, and IR2). In addition, the UI management unit 514 causes the MSI processing unit 511 to create a gray image from the spectral images corresponding to the designated lighting colors (R, IR1, and IR2), and displays the gray image corresponding to the combination of lighting colors after customization in a lower region of the image display region 701.

The user may add a lighting color to the combination of recommended lighting colors. In addition, the user may replace any lighting color included in the combination of recommended lighting colors with another lighting color. Every time the lighting color is changed and the recalculation button 1503 is pressed, the UI management unit 514 causes the MSI processing unit 511 to update the gray image and the calculation unit 561 to update the separation degree. Accordingly, the user can adjust the types and number of lighting colors while confirming the gray image.

The MSI processing unit 511 may create a foreground image by performing color extraction based on the color information of the foreground region, create a background image by performing color extraction based on the color information of the background region, and create a difference image between the foreground image and the background image as the inspection image.

<Summary>

As described above, the illumination device 3 is an example of the illumination unit which includes the plurality of light emitting elements (light sources) that generates illumination beams of mutually different lighting colors, and individually irradiates the target object with the illumination beams of the respective lighting colors. The camera 4 is an example of the imaging unit that receives the light reflected from the object for each illumination beam of each lighting color and generates images (spectral images) of the target object. The display unit 7 is an example of a display unit that displays the images of the target object (the setting target object or the inspection target object). In particular, the display unit 7 is an example of the display unit that displays the image of the setting target object, based on a plurality of spectral images regarding the setting target object. The processor 510 (the MSI processing unit 511, the illumination control unit 512, and the imaging control unit 513) is an example of a control unit that controls the illumination unit to irradiate the setting target object individually with the illumination beams of the respective lighting colors in the predetermined order, and controls the imaging unit to generate a plurality of setting images regarding the setting target object.

As illustrated in FIG. 11 and the like, the UI management unit 514 is an example of a region reception unit which receives designation of at least one of the foreground region and the background region in the image of the setting target object displayed on the display unit.

As illustrated in FIG. 11, the processor 510 functions as a specifying unit that specifies the color information of the foreground color based on color information of a plurality of pixels in the foreground region, and specifies the color information of the background color based on color information of a plurality of pixels in the background region.

The processor 510 (the setting unit 560) is an example of the setting unit that calculates the separation degree between the color information of the foreground color and the color information of the background color for each combination of lighting colors recommended to illuminate the inspection target object out of a plurality of lighting colors, and sets the combination of recommended lighting colors based on the separation degree.

The inspection unit 531 is an example of the inspection unit that inspects the inside of each inspection region in the plurality of generated inspection images regarding the inspection target object illuminated with the illumination beams of the lighting colors according to the combination of the recommended lighting colors set by the setting unit.

In particular, since the image inspection device 8 decides the combination of recommended lighting colors according to the present embodiment, the burden on the user relating to the selection of the lighting color required for image inspection by the multi-spectral imaging is alleviated. The setting target object is the workpiece 2 used to decide the combination of recommended lighting colors, and the inspection target object is the workpiece 2 that is an object to be subjected to the image inspection. The setting target object and the inspection target object may be the same or different from each other. The setting target object may be an inspection-passed product or a reference product.

As described with reference to FIG. 5 and the like, the setting unit 560 may include the calculation unit 561 which calculates the separation degree between the color information of the foreground color and the color information of the background color for each of a plurality of combinations of lighting colors having mutually different number of lighting colors, and the decision unit 562 which decides the combination of recommended lighting colors based on the separation degrees of the respective combinations calculated by the calculation unit 561. In this manner, the combination of recommended lighting colors may be decided based on an index such as the separation degree or an evaluation value.

The lighting color designation unit 517, the pull-down menu 711, and the like are examples of the lighting color number reception unit which receives designation of the number of lighting colors constituting the combination of recommended lighting colors. The calculation unit 561 calculates the separation degree for each of a plurality of combinations of lighting colors corresponding to the number of lighting colors received by the lighting color number reception unit.

The decision unit 562 may decide the combination in which the maximum separation degree is obtained as the combination of recommended lighting colors among the plurality of combinations of lighting colors including lighting colors equal to or smaller than the number received by the lighting color number reception unit. Accordingly, a combination which allows the highest image inspection accuracy may be decided among the combinations corresponding to the number of lighting colors desired by the user.

As illustrated in FIGS. 9 and 10, the text box 712 is an example of the threshold reception unit which receives designation of the threshold (for example, separation degree threshold) relating to separation degree. The decision unit 562 may decide the combination of lighting colors in which the separation degree exceeding the separation degree threshold is obtained and which has the smallest number of lighting colors as the combination of the recommended lighting colors among the plurality of combinations of lighting colors. Accordingly, the lighting pattern in which the separation degree set by the user is obtained and which has the smallest number of light emitting elements to be turned on is used for the image inspection, and thus, it is possible to achieve the inspection accuracy desired by the user while shortening the image inspection time.

When there is no combination of lighting colors in which the separation degree exceeding the threshold is obtained among the plurality of lighting patterns, the decision unit

562 may select the combination of lighting colors having the maximum separation degree among the plurality of combinations of lighting colors and decides this combination as the combination of recommended lighting colors. Accordingly, the combination of lighting colors in which the separation degree the closest to the separation degree designated by the user is achieved is used for the image inspection.

The display unit 7 and the UI management unit 514 may display the separation degree corresponding to the combination of recommended lighting colors. Accordingly, the user can easily confirm the level of the separation degree that can be achieved by the combination of recommended lighting colors. The UI management unit 514 may display the separation degrees for all lighting colors and the separation degree for another combination of lighting colors on the display unit 7 so as to allow easy comparison for the user.

As illustrated in FIG. 11, the region designation unit 516 of the UI management unit 514 may receive designation of both the foreground region and the background region in the image of the setting target object displayed on the display unit.

In addition, the separation degree may be an inter-group distance between a distribution of color information of the foreground group including the plurality of foreground colors registered from the plurality of foreground regions and a distribution of color information of the background group including the plurality of background colors registered from the plurality of background regions.

As described with reference to FIG. 15, the UI management unit 514 may function as an addition and deletion reception unit that receives addition or deletion of a lighting color with respect to the combination of recommended lighting colors when the image of the setting target object or the inspection target object is being displayed. When a type of a lighting color included in the combination of recommended lighting colors is changed, the UI management unit 514 and the MSI processing unit 511 may read spectral images corresponding to the changed combination of recommended lighting colors from the storage device 520 and update the image that is being displayed on the display unit. Accordingly, if a lighting color is added or deleted to or from the combination of recommended lighting colors while the image of the target object is being displayed, the display unit 7 updates the image to an image in which the addition or deletion of the lighting color has been reflected and displays the updated image. Accordingly, the user can execute addition and deletion of the lighting color while confirming the image of the target object.

As described above, the separation degree may be the distance between the color information (foreground color) of the foreground region and the color information (background color) of the background region. The calculation unit 561 calculates the separation degree for each combination of lighting colors. For example, the calculation unit 561 may calculate a separation degree for each of a plurality of pairs, constituted by one of a plurality of foreground colors and one of a plurality of background colors, and decide a minimum separation degree among the separation degrees for the plurality of pairs obtained by the calculation as a separation degree for each lighting pattern. The pair is formed for all combinations between the plurality of foreground colors and the plurality of background colors. Thus, 64 pairs are formed using eight foreground regions and eight background regions.

As described with reference to FIG. 14 and the like, the inspection unit 531 may include the plurality of inspection tools that executes mutually different types of image inspection. The UI management unit 514 receives registration of the registered color and the background color for each inspection tool. Since the combination of the registered color and the background color differs for each inspection tool, the separation degree also differs for each inspection tool. The setting unit 560 may obtain separation degrees for all of the plurality of inspection tools, and decide the combination of recommended lighting colors such that all the separation degrees exceed the threshold. Alternatively, the setting unit 560 may obtain the minimum number of lighting colors having the separation degree exceeding the threshold and types of the lighting color for each of the plurality of inspection tools, and decide a logical sum of the types of obtained lighting colors as the combination of recommended lighting colors. Accordingly, it is possible to reduce the number of lighting colors while maintaining the inspection accuracy for all the inspection tools.

Figure 19:
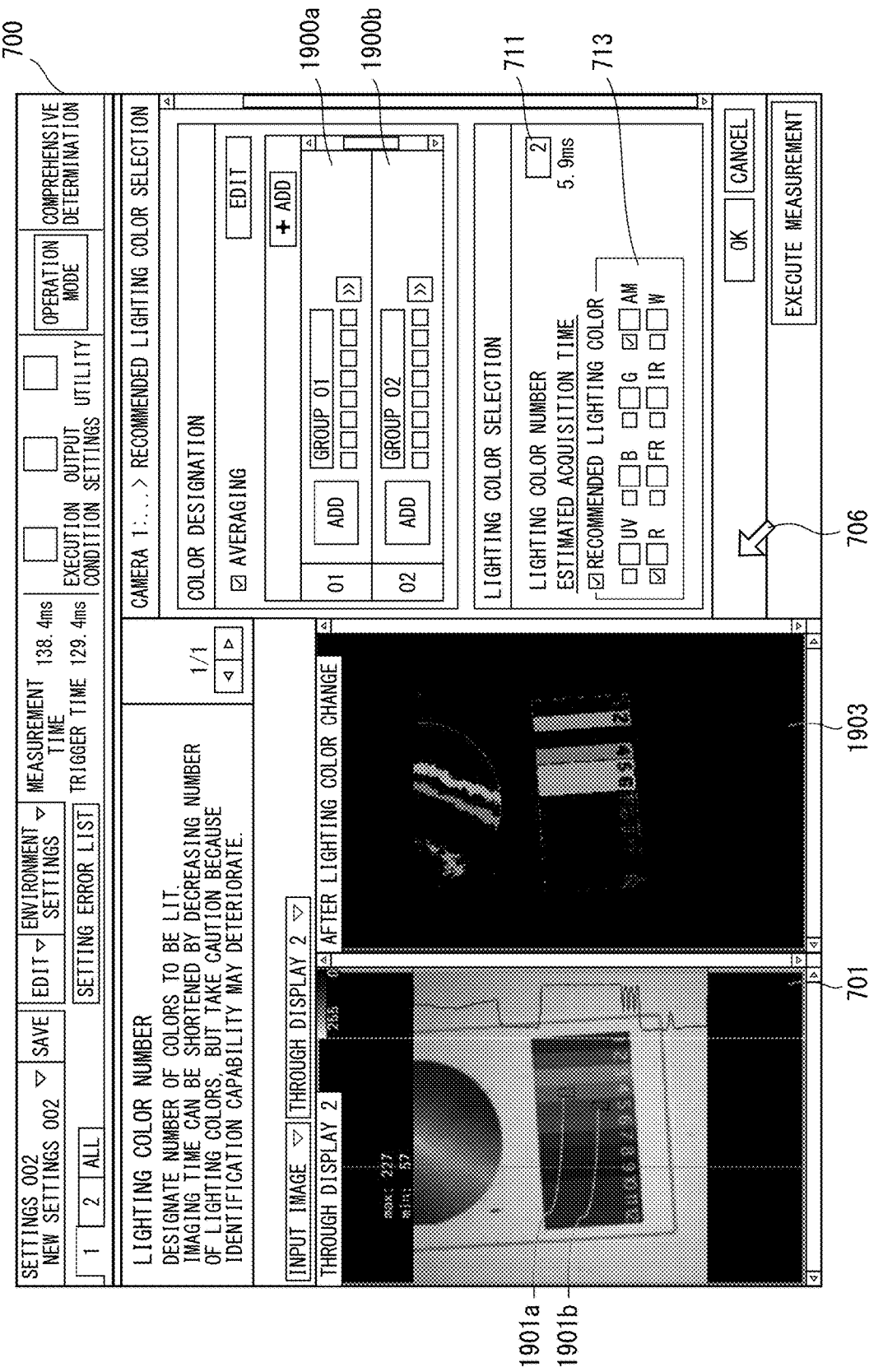
FIG. 19 is a view illustrating a UI that assists selection of a lighting color.
Figure 20:
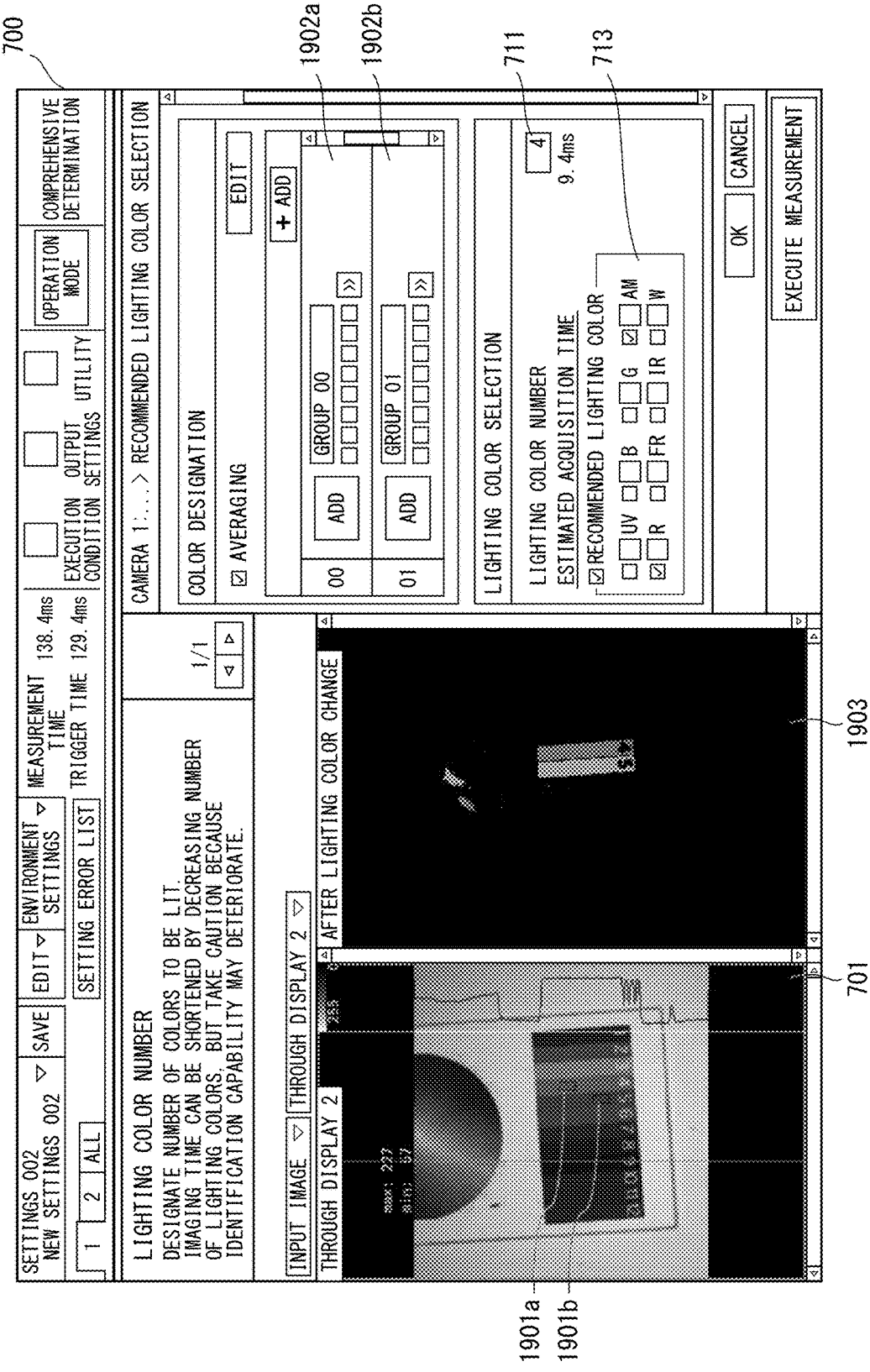
FIG. 20 is a view illustrating a UI that assists selection of a lighting color.

FIGS. 19 and 20 illustrate user interfaces for setting of a lighting color. Elements that have been already described are denoted by the same reference numerals. In this example, an appropriate combination of lighting colors is presented within a range of the number of lighting colors designated by the user such that a separation degree between two color groups (for example, foreground and background) is increased. When the user operates the pointer 706 and presses an add button of a first group 1900a among a plurality of groups, the UI management unit 514 activates a color extraction tool such as a dropper. The UI management unit 514 causes a color of a first region 1901a designated by the operation of the pointer 706 to belong to the first group 1900a. Similarly, when an add button of a first group 1900b is pressed, the UI management unit 514 causes a color of a second region 1901b designated by the operation of the pointer 706 to belong to the first group 1900b. The calculation unit 561 obtains separation degrees according to the number of lighting colors (for example, two) selected by the lighting color number selection unit such as the pull-down menu 711 and the like. The decision unit 562 decides a combination of recommended lighting colors (for example, R and AM) in which the separation degree becomes the maximum. The UI management unit 514 displays the combination of recommended lighting colors on the recommended lighting color display unit 713. As described in relation to the foreground and the background, the MSI processing unit 511 creates an image of a first group and an image of a second group according to the recommended lighting colors, further obtains a difference image therebetween, and displays the difference image on a result display unit 1903 that indicates a color extraction result. Since the number of lighting colors is too small in the case illustrated in FIG. 19, the two color regions that are desirably identified from each other are not sufficiently separated.

FIG. 20 illustrates a case where the user increases the number of lighting colors to four. When the number of lighting colors is changed, the calculation unit 561 obtains separation degrees for each combination of lighting colors according to the number of lighting colors. The decision unit 562 decides a combination of recommended lighting colors (for example, R, AM, B, and FR) having the maximum separation degree. Further, the UI management unit 514 displays the combination of recommended lighting colors on the recommended lighting color display unit 713. The MSI processing unit 511 creates an image of a first group and an image of a second group according to the recommended lighting colors, further obtains a difference image therebetween, and displays the difference image on the result display unit 1903 that indicates the color extraction result. Since the number of lighting colors is sufficient in the case illustrated in FIG. 20, the two color regions that are desirably identified from each other are sufficiently separated. In this manner, the user can decide the number of lighting colors while viewing the color extraction result.

The UI management unit 514 may calculate and display an estimated acquisition time which is a processing time required to create one inspection image by the calculation unit 561 or the like. In general, the inspection time that can be allocated to one workpiece is finite. Therefore, the user can decide the number of lighting colors such that the estimated acquisition time falls within the inspection time.

What is claimed is:

1. An image inspection device comprising:
an illumination unit which includes a plurality of light emitting elements that generates illumination beams mutually having different lighting colors and individually irradiates a target object with the illumination beams of the respective lighting colors;
an imaging unit which receives light reflected from the target object for each of the illumination beams of the lighting colors and generates a spectral image of the target object;
a control unit which controls the illumination unit to irradiate the target object sequentially with the illumination beams of the respective lighting colors and controls the imaging unit to generate a plurality of the spectral images;
a display unit which displays an image of the target object based on the plurality of spectral images of the target object;
a region reception unit which receives designation of a foreground region and a background region in the image of the target object displayed on the display unit;
a specifying unit which specifies color information of a foreground color based on color information of a pixel in the foreground region and specifies color information of a background color based on color information of a pixel in the background region;
a setting unit which calculates a separation degree between the color information of the foreground color and the color information of the background color for each of combinations of lighting colors recommended for illumination of an inspection target object out of the plurality of lighting colors, and sets a combination of recommended lighting colors based on the separation degree; and
an inspection unit which inspects an inside of an inspection region in an inspection image generated for the inspection target object illuminated by illumination beams of lighting colors according to the combination set by the setting unit.

2. The image inspection device according to claim 1, wherein
the setting unit includes
a calculation unit which calculates the separation degree between the color information of the foreground color and the color information of the background color for each of a plurality of combinations of lighting colors having mutually different number of lighting colors, and
a decision unit which decides the combination of recommended lighting colors based on the separation degrees of the respective combinations calculated by the calculation unit.

3. The image inspection device according to claim 2, further comprising a lighting color number reception unit which receives designation of a number of lighting colors constituting the combination of recommended lighting colors,
wherein the calculation unit calculates the separation degree for each of the plurality of combinations of lighting colors corresponding to the number of lighting colors received by the lighting color number reception unit.

4. The image inspection device according to claim 3, wherein the decision unit decides a combination in which a maximum separation degree is obtained as the combination of recommended lighting colors among the plurality of combinations of lighting colors including lighting colors equal to or smaller than the number received by the lighting color number reception unit.

5. The image inspection device according to claim 2, further comprising a threshold reception unit which receives designation of a threshold relating to the separation degree,
wherein the decision unit decides a combination of lighting colors in which a separation degree exceeding the threshold is obtained and which has a smallest number of lighting colors as the combination of recommended lighting colors.

6. The image inspection device according to claim 5, wherein when there is no combination of lighting colors in which the separation degree exceeding the threshold is obtained among the plurality of combinations of lighting colors, the decision unit selects a combination of lighting colors having a maximum separation degree among the plurality of combinations of lighting colors and decides the selected combination as the combination of recommended lighting colors.

7. The image inspection device according to claim 1, wherein the display unit displays a separation degree corresponding to the combination of recommended lighting colors.

8. The image inspection device according to claim 1, wherein
the control unit generates a foreground image and a background image from the plurality of spectral images acquired by sequentially and individually irradiating the inspection target object with illumination beams of a plurality of lighting colors constituting the combination of recommended lighting colors, and
the display unit displays a difference image between the foreground image and the background image as the inspection image.

9. The image inspection device according to claim 1, further comprising an addition and deletion reception unit which receives addition or deletion of a lighting color with respect to the combination of recommended lighting colors.

10. The image inspection device according to claim 1, wherein the region reception unit receives designation for both the foreground region and the background region in the image of the target object displayed on the display unit.

11. The image inspection device according to claim 1, wherein the separation degree is an inter-group distance between a distribution of color information of a foreground group including a plurality of foreground colors registered from a plurality of foreground regions and a distribution of color information of a background group including a plurality of background colors registered from a plurality of background regions.

12. The image inspection device according to claim 2, wherein the calculation unit calculates a separation degree for each of a plurality of pairs, constituted by one of a plurality of foreground colors and one of a plurality of background colors, and decides a minimum separation degree among the separation degrees of the plurality of pairs as a separation degree for each of the combinations of lighting colors.

13. The image inspection device according to claim 1, wherein
the inspection unit includes a plurality of inspection tools each of which executes different image inspection, and
the setting unit obtains the separation degrees for all of the plurality of inspection tools and decides the combination of recommended lighting colors such that all the separation degrees exceed a threshold.

14. The image inspection device according to claim 1, wherein
the inspection unit includes a plurality of inspection tools each of which executes different image inspection, and
the setting unit obtains a minimum number of lighting colors and types of the lighting colors in which the separation degree exceeds a threshold for each of the plurality of inspection tools, and decides a logical sum of the obtained types of lighting colors as the combination of recommended lighting colors.

15. An image inspection device comprising:
an illumination unit which includes a plurality of light emitting elements that generates illumination beams mutually having different lighting colors and individually irradiates a target object with the illumination beams of the respective lighting colors;
an imaging unit which receives light reflected from the target object for each of the illumination beams of the lighting colors and generates a spectral image of the target object;
a control unit which controls the illumination unit to irradiate the target object sequentially with the illumination beams of the respective lighting colors and controls the imaging unit to generate a plurality of the spectral images;
a display unit which displays an image of the target object based on the plurality of spectral images of the target object;
a region reception unit which receives designation of at least one of a foreground region and a background region in the image of the target object displayed on the display unit;
a specifying unit which specifies color information of a foreground color and color information of a background color by specifying color information of the one region based on color information of a pixel in the one region and specifying color information different from the color information of the one region as color information of the other region;
a setting unit which calculates a separation degree between the color information of the foreground color and the color information of the background color for each of combinations of lighting colors recommended for illumination of an inspection target object out of the plurality of lighting colors, and sets a combination of recommended lighting colors based on the separation degree; and
an inspection unit which inspects an inside of an inspection region in an inspection image generated for the inspection target object illuminated by illumination beams of lighting colors according to the combination set by the setting unit.

* * * * *